(12) United States Patent
Linot

(10) Patent No.: US 11,771,600 B2
(45) Date of Patent: Oct. 3, 2023

(54) LAMINATED ASSEMBLY, NAPPY COMPRISING SUCH AN ASSEMBLY AND METHOD FOR MANUFACTURING SUCH AN ASSEMBLY

(71) Applicant: APLIX, Le Cellier (FR)

(72) Inventor: Pierre-Yves François Jean Linot, Le Cellier (FR)

(73) Assignee: APLIX, Le Cellier (FR)

( * ) Notice: Subject to any disclaimer, the term of this patent is extended or adjusted under 35 U.S.C. 154(b) by 0 days.

(21) Appl. No.: 16/981,241

(22) PCT Filed: Mar. 20, 2019

(86) PCT No.: PCT/FR2019/050638
§ 371 (c)(1),
(2) Date: Sep. 15, 2020

(87) PCT Pub. No.: WO2019/180381
PCT Pub. Date: Sep. 26, 2019

(65) Prior Publication Data
US 2021/0045931 A1 Feb. 18, 2021

(30) Foreign Application Priority Data

Mar. 21, 2018 (FR) ...................................... 1852405

(51) Int. Cl.
*A61F 13/15* (2006.01)
*A61F 13/49* (2006.01)
(52) U.S. Cl.
CPC .. *A61F 13/15699* (2013.01); *A61F 13/15731* (2013.01); *A61F 13/15756* (2013.01); *A61F 13/4902* (2013.01); *A61F 13/49015* (2013.01)
(58) Field of Classification Search
CPC ......... A61F 13/15699; A61F 13/15731; B32B 7/12; B32B 7/15; B32B 5/022
See application file for complete search history.

(56) References Cited

U.S. PATENT DOCUMENTS

| 2003/0232556 A1* | 12/2003 | Toro ...................... A61F 13/145 |
| | | 442/286 |
| 2013/0149488 A1 | 6/2013 | Chandrasekaran |
| 2020/0164610 A1* | 5/2020 | Davis ...................... B32B 27/32 |

FOREIGN PATENT DOCUMENTS

| CN | 1756493 A | 4/2006 |
| CN | 102894550 A | 1/2013 |

(Continued)

OTHER PUBLICATIONS

International Search Report and Written Opinion dated Jun. 11, 2019 in counterpart International Patent Application No. PCT/FR2019050638 (15 pages).

(Continued)

*Primary Examiner* — George R Koch
*Assistant Examiner* — Christopher C Caillouet
(74) *Attorney, Agent, or Firm* — Bookoff McAndrews, PLLC

(57) ABSTRACT

The invention relates to a laminated assembly including a support layer (32) and an anti-slip strip (34), the anti-slip strip (34) including an elastomeric material, the support layer (32) and the anti-slip strip (34) being laminated together, the anti-slip strip (34) including a base (34A) and a plurality of protruding elements (34B) extending from the base (34A) and the plurality of protruding elements (34B) protruding from a face (30A) of the laminated assembly (30). The invention also relates to a diaper including such a laminated assembly (30) and a process for manufacturing the laminated assembly (30). The invention also relates to a diaper including such an assembly and a process for manufacturing such an assembly.

20 Claims, 12 Drawing Sheets

(56) References Cited

FOREIGN PATENT DOCUMENTS

| | | |
|---|---|---|
| CN | 107635747 A | 1/2018 |
| EP | 1311372 B1 | 5/2003 |
| FR | 2943356 A1 | 9/2010 |
| JP | 2013-533770 A | 8/2013 |
| WO | 2014190042 A1 | 11/2014 |
| WO | 2016/149243 A1 | 9/2016 |
| WO | 2017187097 A1 | 11/2017 |
| WO | 2017187103 A1 | 11/2017 |

OTHER PUBLICATIONS

Search Report issued in Chinese Patent Application No. 201980020940.8, dated Jul. 29, 2021 (2 pages).
Office Action issued in Chinese Patent Application No. 201980020940.8, dated Aug. 4, 2021, with English translation (19 pages).
Notice of Reasons for Refusal issued in Japanese Patent Application No. 2020-550728 dated Jan. 20, 2023 (6 pages).

\* cited by examiner

LAMINATED ASSEMBLY, NAPPY COMPRISING SUCH AN ASSEMBLY AND METHOD FOR MANUFACTURING SUCH AN ASSEMBLY

CROSS-REFERENCE TO RELATED APPLICATION(S)

This patent application is a national stage entry of International Patent Application No. PCT/FR2019/050638, filed on Mar. 20, 2019, which claims the benefit of priority to French Patent Application No. 1852405, filed on Mar. 21, 2018, the entirety of which is incorporated herein by reference.

TECHNOLOGICAL FIELD

The present disclosure relates to laminated assemblies which may be used in the field of hygiene, in particular absorbent articles, notably for the manufacture of elastic ears for diapers.

TECHNOLOGICAL BACKGROUND

A disposable diaper is generally composed of an absorbent central portion comprising at each end a front waistband portion having two front ears and a back waistband portion having two back ears for attaching the diaper to the disposable diaper's wearer. Each back ear is generally provided with a retaining device, for example with hooks, which cooperates with an application zone arranged on the front belt. In the hygiene field, this application zone is commonly referred to as the "landing zone" or in French to the "bande confort".

However, the diaper may sag at the ears and/or the front ear may move relative to the back ear due to the movements of the diaper wearer. This sagging and/or displacement may result in discomfort to the diaper wearer and/or unwanted leaks.

Presentation

The present disclosure is intended to remedy at least some of these drawbacks.

To this end, the present disclosure relates to a laminated assembly including a support layer and an anti-slip strip, the anti-slip strip including an elastomeric material, the support layer and the anti-slip strip being laminated together, the anti-slip strip including a base and a plurality of protruding elements extending from the base and the plurality of protruding elements protruding from one face of the laminated assembly.

By virtue of the anti-slip strip, and in particular the protruding elements, when the laminated assembly is in contact with another surface, the displacement of this other surface with respect to the anti-slip strip is reduced. However, the protruding elements do not allow the anti-slip strip to be joined and hooked with this other surface. For example, the anti-slip strip is such that it is not possible to suspend a weight of 1 kg (kilogram) for a period of 10 seconds. In certain cases, the anti-slip strip has a 180° peel force which is less than or equal to 0.02 N, in certain cases equal to 0 N.

The direction MD refers to the machine direction and means the direction of travel of the anti-slip strip in the machine during the manufacture of the anti-slip strip, and the direction CD refers to the cross direction and means the direction perpendicular to the direction MD.

The "180° peel" method is a method for measuring the peeling force, i.e. the force to separate the laminated assembly from the application zone. This method is described below.

Specimen conditioning—Test specimens are conditioned for 2 hour (hour) at 23° C.±2° C. with 50%±5% relative humidity.

Preparation of the anti-slip strip—The anti-slip strip is generally used in the direction MD. The anti-slip strip is usually in the form of a tape, the length of which is in the direction MD. A portion of the tape in the direction MD is bonded to 80 g/cm$^2$ paper and a 2 kg (kilograms) roller is applied or rotated on the anti-slip strip in one direction and then in the other (back and forth) along the entire length of the portion of the tape at a speed of about 700 mm/min (millimeters per minute). The paper and the anti-slip strip are cut with a pair of scissors into strips 25.4 mm (millimeters) wide in the direction MD. Each paper strip has a length of 210 mm and the anti-slip strip is placed in the center of the strip.

Preparation of the application zone—The application zone specimen has a width of 50 mm in the direction MD and the length is a maximum of 200 mm and the specimen is cut in half lengthwise.

Assembly—The strip is placed on the application zone specimen so that the anti-slip strip is centered on the application zone specimen. The 2 kg (kilograms) roller is applied or rotated over the strip in one direction and then in the other (back and forth) along the entire length of the strip at a speed of about 700 mm/min. The application zone specimen is placed in a clamp of a bracket with the cut side in the clamp and a 1 kg weight is suspended from the lower part of the strip for 10 s (seconds). The weight is then removed. This step ensures that the anti-slip strip and the application zone specimen are assembled.

Measurement—The assembly is then placed in a tensile testing machine with a 100 N (newton) measuring cell. The strip is inserted into the upper (movable) jaw. The reading of the force measuring cell is set to zero. The application zone specimen is inserted into the lower jaw (fixed) and a slight tension is created. The force must be between 0.02 N and 0.05 N. During insertion, the jaws are spaced 50 mm apart. The assembly is centered between the two jaws. The test is carried out at constant displacement at a speed of 305 mm/min and the test stroke is 50 mm. This test stroke is adapted according to the width of the retaining device to be tested.

Since the anti-slip strip is made of elastomeric material, the anti-slip strip is elastic. The elasticity of the anti-slip strip gives elasticity to the laminated assembly. Thus, when using the laminated assembly, the laminated assembly may be stretched, with the anti-slip strip itself being stretched. Stretching of the laminated assembly allows a pressure to be exerted, for example when attaching a disposable diaper to a wearer, that is greater than the pressure that would be exerted by the laminated assembly if it were not stretched. This higher pressure also reduces the risk of the surface in contact with the anti-slip strip moving and/or shifting relative to the anti-slip strip.

As the anti-slip strip is made of elastomeric material, it is soft to the touch for both the wearer and the person handling the diaper and minimizes the risk of skin sensitization.

As non-limiting examples of elastomeric materials, mention may be made of: styrene/isoprene (SI), styrene/isoprene/styrene (SIS), styrene/butadiene/styrene (SBS), styrene-ethylene/butylene-styrene (SEBS), styrene-ethylene/propylene-styrene (SEPS) or SIBS copolymers. Mixtures of these elastomers with each other or with non-elastomers modifying certain characteristics other than elasticity may also be taken into account. For example, up to 50% by weight (or by mass) but preferably less than 30% by weight (or by mass) of polymer may be added in order to modify certain characteristics of the base materials (elasticity, heat resistance, processability, UV resistance, coloring, etc.), such as polyvinyl styrene, polystyrenes or poly a-methyl styrene, epoxy polyesters, polyolefins, for example polyethylenes or certain ethylene/vinyl acetates, preferably those of high molecular weight (higher molar mass).

The elastomeric material may be, in particular, a styrene-isoprene-styrene, available for example from the firm Kraton Polymers, under the name KRATON D (registered trademark), or from the firm DEXCO POLYMERS LP under the name VECTOR SBC 4211 (registered trademark). Thermoplastic elastomer (TPE) materials, in particular a thermoplastic polyurethane elastomer, including PELETHANE (registered trademark) 2102-75A from The Dow Chemical Company, may also be used. A styrene-butadiene-styrene may also be used, including KRATON D-2122 (registered trademark) from Kraton Polymers or VECTOR SBC 4461 (registered trademark) from Dexco Polymers LP. Alternatively, styrene-ethylene/butylene, including KRATON G-2832 (registered trademark) from Kraton Polymers, or a styrene-ethylene-butylene-styrene (SEBS) block copolymer, including KRATON (registered trademark) G2703.

The list, without being exhaustive, may be completed by the use of all hydrogenated polyisoprene polymers such as styrene-ethylene-propylene-styrene (SEPS), styrene-ethylene-propylene-styrene-ethylene-ethylene-propylene (SEP-SEP), hydrogenated polybutadiene polymers such as styrene-ethylene-butylene-styrene (SEBS), styrene-ethylene-butylene-styrene-ethylene-butylene-ethylene-butylene (SEBSEB), styrene-butadiene-styrene (SBS), styrene-isoprene-styrene (SIS), styrene-isoprene-butadiene-styrene (SIBS), hydrogenated polyisoprene/butadiene polymer such as styrene-ethylene-ethylene-ethylene-epropylene-styrene (SEEPS), and commercially available vinyl-hydrogenated polyisoprene/hydrogenated polyisoprene/polyisoprene/polystyrene triblock polymers, such as HYBRAR 7311 (Kuraray America, Inc., Houston, Tex.), and their combinations.

Polymer block configurations such as diblock, triblock, multiblock, star and radial are also considered in the present disclosure. In some cases, higher molecular weight (or molar mass) block copolymers may be desirable. Block copolymers are available from Kraton Polymers U.S. LLC of Houston, Tex. under the designations, for example, Kraton MD6716, Kraton D1102, Kraton SIBS D1102, Kraton D1184, Kraton FG1901 and Kraton FG1924, and Septon Company of America, Pasadena, Tex. under the designations Septon 8007, Septon V9827 and Septon 9618. Dynasol of Spain is another potential supplier of these polymers. In particular, the Kraton MD6716 SEBS triblock polymer is particularly suitable for the present disclosure.

A copolymer of isooctyl acrylate and acrylic acid in monomer ratios of 90/10, which is a thermoplastic with physical crosslinking in the absence of a crosslinker, may also be used. A polyamide polyester block copolymer PEBAX (registered trademark) 2533 from Arkema may also be used.

Other possible materials are polyolefin polymers, mainly copolymers of ethylene and/or propylene, with elastomer characteristics, especially from metallocene catalysis, such as VISTAMAXX VM-1120 (registered trademark), available from Exxon Mobil Chemical, or rubber-filled polymers, such as EPDM-filled Santoprene.

Examples of polyolefin-based thermoplastic elastomers suitable for use in elastomeric film layers include, inter alia, a crystalline polyolefin, for example, a homopolymer or copolymer of an alpha-olefin having 1 to 20 carbon atoms, and comprising 1 to 12 carbon atoms.

The homopolymers and the copolymers described below are examples of crystalline polyolefins.

(1) Ethylene homopolymer Ethylene homopolymer may be prepared by any of the low-pressure and high-pressure processes.

(2) Copolymers of ethylene and not more than 10 mole % of alpha-olefins other than ethylene or vinyl monomers such as vinyl acetate and ethyl acrylate; for example, ethylene octene copolymer, available under the brand names Engage 8407 or Engage 8842 (Dow Chemical, Houston, Tex.).

(3) Propylene homopolymer; examples include polypropylene impact copolymer PP7035E4 and polypropylene random copolymer PP9574E6 (Exxon Mobil, Houston, Tex.).

(4) Random copolymers of propylene and not more than 10 mole % of alpha-olefins-olefins other than propylene.

(5) Block copolymers of propylene and not more than 30 mol % of alpha-olefins other than propylene.

(6) Homopolymer of butene-1-butene.

(7) Random copolymers of 1-butene and not more than 10 mole % of alpha-olefins-olefins other than 1-butene.

8) 4-methyl-1-pentene homopolymer 4-methyl-1-pentene homopolymer (9) Random copolymers of 4-methyl-1-pentene and not more than 20 mol % of alpha-olefins other than 4-methyl-1-pentene.

Alpha-olefins include, for example, ethylene, propylene, butene-1, 4-methyl-1-pentene, 1-hexene and 1-octene.

Commercially available thermoplastic elastomers based on polyolefins for use in elastomer film layers include VISTAMAXX™ (propylene-based elastomer, available from ExxonMobil Chemical, Houston, Tex.), INFUSE™ (olefin block copolymers, available from Dow Chemical Company, Midland, Mich.), VERSIFY™ (propylene-ethylene copolymers) such as VERSIFY™ 4200 and VERSIFY™ 4300 (Dow Chemical Company, Midland, Mich.), ENGAGE™ (ethylene octane copolymer, available from Dow Chemical, Houston, Tex.) and NOTIO 0040 and NOTIO 3560 (available from Mitsui Chemical (USA), New York, N.Y.), Adflex X100 G (available from Lyondellbasell).

In a particularly adapted embodiment, the thermoplastic elastomer based on polyolefin is VISTAMAXX™ 6102FL or VISTAMAXX 7050 FLX (available from ExxonMobil Chemical, Houston, Tex.). The notation "™" for registered brand names corresponds to "trademark".

In another case, the thermoplastic elastomer may be a thermoplastic ester/ether elastomer or thermoplastic polyurethanes.

Elastomeric material means a material which may be stretched without breaking under the effect of a stretching force exerted in a given direction and which may substantially recover its original shape and dimensions after release of this stretching force. It is for example a film which retains a residual deformation or remanence after elongation and release (residual deformation also called "permanent set" or "SET") less than or equal to 30%, preferably less than or equal to 20%, even more preferably less than or equal to 10%, of its initial dimension (before elongation) for an elongation of 100% of its initial dimension, at room temperature (23° C.—degrees Celsius). The elastomeric material may be a thermoplastic elastomeric material, in particular a physically crosslinked thermoplastic elastomeric material, such as those described in the present disclosure, or a chemically crosslinked thermoplastic elastomeric material.

In certain embodiments, the anti-slip strip has a residual deformation of less than or equal to 30%, preferably less than or equal to 20%, even more preferably less than or equal to 15%, even more preferably less than or equal to 10% of its initial dimension (before elongation) for an elongation of 100% of its initial dimension, at room temperature (23° C.).

In certain embodiments, the laminated assembly has a residual deformation less than or equal to 30%, preferably less than or equal to 20%, even more preferably less than or equal to 15%, even more preferably less than or equal to 10% of its initial dimension (before elongation) for an elongation of 100% of its initial dimension, at room temperature (23° C.).

In certain embodiments, the support layer consists of a nonwoven web.

Nonwoven web means a product obtained by the formation of a web of fibers and/or filaments which have been consolidated. Consolidation may be mechanical, chemical or thermal and involves the presence of a bond between the fibers and/or filaments. This consolidation may be direct, i.e. made directly between the fibers and/or filaments by welding, or it may be indirect, i.e. through an intermediate layer between the fibers and/or filaments, for example a layer of adhesive or a layer of binder. The term nonwoven refers to a ribbon- or web-like structure of fibers and/or filaments which are interlaced in a non-uniform, irregular or random manner. A nonwoven may be made from various synthetic and/or natural materials. Examples of natural materials are cellulose fibers such as cotton, jute, flax and the like and may also include reprocessed cellulose fibers such as rayon or viscose. Natural fibers for a nonwoven web may be prepared using various processes such as carding. Examples of synthetic materials include, but are not limited to, synthetic plastic polymers, which are known to form fibers which include, but are not limited to, polyolefins, for example, polyethylene, polypropylene, polybutylene and the like; polyamide, for example, polyamide 6, polyamide 6.6, polyamide 10, polyamide 12 and the like; polyesters, for example polyethylene terephthalates, polybutylene terephthalates, polylactic acids and the like, polycarbonates, polystyrenes, thermoplastic elastomers, vinyl polymers, polyurethanes and blends and co-polymers thereof.

In certain embodiments, the support layer may have a single layer structure or a multilayer structure. The support layer may also be combined with another material to form a laminate. For example, the nonwoven may be a nonwoven of the Spunbond, Spunmelt, thermobonded carded type, and the support layer may be SMS, SMMS, SS, SSS, SSMMS, SSMMMS, Air through or other. These examples are given in a non-limiting manner.

A nonwoven web is for example formed from a web of fibers and/or filaments produced by Dry-laid (dry method), Wet-laid (wet method) or Spun-laid technology (melted/extruded method) and consolidated by mechanical, thermal, chemical and/or adhesive bonding.

The nonwoven web may be a calendered carded nonwoven.

The calendered carded nonwoven is a nonwoven comprising a fiber web having web consolidation points distributed substantially homogeneously over the web by thermal consolidation. The consolidation ensures a certain cohesion of the fibers allowing their handling and transport, in particular their winding into reels and unwinding. The activation of the calendered carded nonwoven web makes it possible to lengthen and/or break the fibers of the nonwoven web and/or to deform the consolidation points of the web. The elongation capacity of the nonwoven web is thus increased.

The fibers of the calendered carded nonwoven web are comprised between 1 and 8 dTex (deciTex), preferably between 1.3 and 6.7 dTex, more preferably between 1.6 and 5.5 dTex.

Tex is the SI unit of fineness of textile fibers. It expresses the weight in grams of 1000 m (meters) of fiber length.

In certain embodiments, the support layer may include a nonwoven web forming an acquisition veil, in particular an acquisition veil for an absorbent article.

In certain embodiments, the carrier layer may include a thermoplastic film.

Thermoplastic film means a film of thermoplastic material which may be an elastic or a non-elastic material.

Thermoplastic film of elastic material means a film which may be stretched without breaking under the effect of a stretching force exerted in a given direction and which may substantially recover its original shape and dimensions after release of this stretching force. It is for example a film which retains a residual deformation or remanence after elongation and release (residual deformation also called "permanent set" or "SET") less than or equal to 30%, preferably less than or equal to 20%, even more preferably less than or equal to 10%, of its initial dimension (before elongation) for an elongation of 100% of its initial dimension, at room temperature (23° C.).

Thermoplastic film of non-elastic material means a film which does not fall within the definition of a thermoplastic film of elastic material.

When the thermoplastic film is made of non-elastic material, the elasticity of the laminated assembly is imparted by the elastomeric material of the anti-slip strip, for example by using a nonwoven fabric with a grammage of less than 30 g/m$^2$ (grams per square meter).

As non-limiting examples of thermoplastic material, mention may be made of a polyolefin, polyethylene, linear low-density polyethylene (LLDPE), low-density polyethylene (LDPE), metallocene polyethylene (m-PE), high-density polyethylene (HDPE), EVA (ethylene vinyl acetate) and PP (polypropylene), comprising a monomodal or multimodal (for example bimodal) molecular weight (molar mass) distribution, in particular a composition comprising LLDPE and a plastomer, in particular a polyethylene-based plastomer. Polyamide (PA), polyactic acid (PLA), polyhydroxyalkanoates (PHA), PVOH, PBS, polyester, polyvinyl chloride (PVC) or acrylonitrile butadiene styrene (ABS) could also be used.

In certain embodiments, the thermoplastic film is an elastic film.

As a non-limiting example of elastomeric material for forming the elastic film, mention may be made of the same materials as the elastomeric materials cited as non-limiting examples of elastomeric material for making the anti-slip strip.

In certain embodiments, the elastic film may be formed by an elastic adhesive.

In certain embodiments, the elastic film may include more than one layer or be a "skin layer", i.e. an elastic film covered by a skin.

In certain embodiments, the elastic film may be formed by an elastomeric adhesive.

In certain embodiments, the elastomeric adhesive film may be extruded onto the nonwoven web and then laminated with the nonwoven web.

In certain embodiments, the support layer consists of a nonwoven web and the elastic film.

In certain embodiments, the base of the anti-slip strip and the elastic film each have a width, the width of the base being less than the width of the elastic film, preferably the width of the base being greater than or equal to 10% of the width of the elastic film and less than or equal to 60% of the width of the elastic film.

In certain embodiments, the area of the protruding elements of the anti-slip strip and the base of the anti-slip strip each have a width, the width of the area of the protruding elements being less than the width of the base of the anti-slip strip, preferably less than or equal to 60% of the width of the base, even more preferably less than or equal to 45% of the width of the base.

In certain embodiments, the support layer may include a first nonwoven web, a second nonwoven web and the elastic film, the elastic film being laminated between the first and second nonwoven webs.

In certain embodiments, at rest, in a zone including the protruding elements, the anti-slip strip has a coefficient of static friction, measured according to ASTM D1894, in the direction MD and/or the direction CD, greater than or equal to 0.1, preferably greater than or equal to 0.5, even more preferably greater than or equal to 0.8 and less than or equal to 10, preferably less than or equal to 5, even more preferably less than or equal to 3.

"At rest" means that the laminated assembly is not subject to external forces, such as stretching forces. In other words, "at rest" means that the laminated assembly is tested as it is before the first use by the end user, for example, in the field of diapers, just after packaging, i.e. just before placing the diaper on a person. The measurement of the static coefficient of friction may be carried out in a longitudinal direction and/or a lateral direction, the lateral direction being orthogonal to the longitudinal direction. The measurement of the static coefficient of friction may be carried out in a direction MD and/or a direction CD.

The direction MD refers to the machine direction and means the direction of travel of the anti-slip strip in the machine during the manufacture of the anti-slip strip, and the direction CD refers to the cross direction and means the direction perpendicular to the direction MD.

In certain embodiments, the anti-slip strip has a static coefficient of friction, measured according to ASTM D1894, when the anti-slip strip is stretched to 15% of the value at rest, comprised between 50% and 150% of the static coefficient of friction at rest.

The measurement of the static coefficient of friction may be carried out in a longitudinal direction and/or a lateral direction, the lateral direction being orthogonal to the longitudinal direction. The measurement of the static coefficient of friction may be carried out in a direction MD and/or a direction CD.

The anti-slip strip has a dimension in the direction MD that is larger than a dimension in the direction CD.

In certain embodiments, the anti-slip strip has a grammage per unit area greater than or equal to 10 g/m² (grams per square meter), preferably greater than or equal to 20 g/m² and less than or equal to 250 g/m², preferably less than or equal to 200 g/m².

In certain embodiments, the support layer is bonded together by adhesive bonding.

The adhesive may be applied continuously in a longitudinal direction and discontinuously in a lateral direction. The adhesive thus forms a plurality of adhesive lines, for example continuous in the longitudinal direction. Of course, the width of the adhesive lines and their lateral spacing may be adapted.

In order to measure the characteristics of the elastomeric material, the support layer may be separated from the elastomeric material by using, for example, acetone and/or ethyl acetate.

The elastic film may be formed by an elastic adhesive.

The elastic adhesive film may then be extruded onto the nonwoven web and then laminated with the nonwoven web. The activated zone may extend over the entire length of the nonwoven web measured in the longitudinal direction.

In certain embodiments, the support layer is assembled by ultrasonic welding.

In the manufacture of laminated assemblies, ultrasonic welding is carried out by passing the support layer between two rollers, one of which is a sonotrode. The two rollers, one of which is a sonotrode, apply a force to the support layer perpendicular to the general plane defined by the support layer so that during the ultrasonic welding the support layer is laminated.

In certain embodiments, the support layer is joined by two processes selected from the following list: ultrasonic welding, high-frequency welding, gluing or direct lamination (also called hot lamination).

In certain embodiments, at rest, the plurality of protruding elements has a density of protruding elements greater than or equal to 3 protruding elements per cm², preferably greater than or equal to 10 protruding elements per cm² and less than or equal to 400 protruding elements per cm², preferably less than or equal to 300 protruding elements per cm².

In certain embodiments, at rest, the plurality of protruding elements have a pattern including a repetition of an anti-slip strip pattern, the anti-slip strip pattern extending across a width of the anti-slip strip.

The anti-slip strip has a dimension in the direction MD that is larger than a dimension in the direction CD.

In certain embodiments, a sum of the areas defined on the base by the orthogonal projections of the protruding elements on the base is greater than or equal to 1% of the total area of the base of the anti-slip strip pattern, preferably greater than or equal to 5% and less than or equal to 60% of the total area of the base of the anti-slip strip pattern, preferably less than or equal to 40%, more preferably less than or equal to 35%.

In certain embodiments, the base has a thickness greater than or equal to 10 μm, preferably greater than or equal to 15 μm and less than or equal to 200 μm, preferably less than or equal to 150 μm.

In certain embodiments, the thickness of the base is variable.

In certain embodiments, the protruding elements have a variable width.

The width of the protruding elements is measured in a plane parallel to the plane XY of the base. The width of the protruding elements is measured at the point of the protruding element with the maximum width.

In certain embodiments, the protruding elements may include protruding elements with different heights and/or different widths measured in a plane parallel to the plane XY.

In certain embodiments, the protruding elements are pins and/or studs and/or stems, each stem having a head at one end of the stem opposite the base.

The head is arranged at one end of the protruding element opposite to the base, in particular at the upper face of the base.

"Pin" means a shape without a head or overhang and having a maximum height greater than or equal to a maximum width. "Stud" means a shape with a maximum height less than a maximum width. Pins, studs or stems have a portion with a constant cross-section or a portion with a decreasing cross-section, the decrease facing away from the base.

In certain embodiments, the protruding elements have a height, in a direction perpendicular to the base, greater than or equal to 0.05 mm (millimeter), preferably greater than or equal to 0.10 mm and less than or equal to 0.80 mm, preferably less than or equal to 0.50 mm.

In certain embodiments, at rest, a width of the anti-slip strip is greater than or equal to 5% of a total width of the laminated assembly, preferably greater than or equal to 10% and less than or equal to 45%, preferably less than or equal to 30%.

These values are suitable, for example, for applications for baby or child diapers or adult incontinence diapers.

In certain embodiments, at rest, the width of the anti-slip strip is comprised between 25% and 75% of the total width of the laminated assembly.

These values are suitable, for example, for applications for absorbent articles, for example baby or child diapers or adult incontinence pants or feminine hygiene articles. These values may be measured once the absorbent article is assembled.

In certain embodiments, at rest, the width of the anti-slip strip is comprised between 55% and 100% of the total width of the laminated assembly.

These values are suitable, for example, for applications for absorbent articles, for example, feminine hygiene articles. These values may be measured once the absorbent article is assembled.

In certain embodiments, the support layer penetrates at least partially into the base of the anti-slip strip, for example the support layer is bonded by direct lamination to the anti-slip strip.

In certain embodiments, the anti-slip strip is bonded to the support layer.

In certain embodiments, the anti-slip strip is welded to the support layer by ultrasonic welding.

In certain embodiments, the anti-slip strip and the elastic film are made of the same elastomeric material.

In certain embodiments, the anti-slip strip and the elastic film are made of different elastomeric materials.

In certain embodiments, the nonwoven web is activated before and/or after bonding with the elastic film.

In certain embodiments, the base of the anti-slip strip may include two edges in a longitudinal direction, one of said edges having hills and valleys, wherein a maximum deviation between the hills and valleys in a lateral direction, orthogonal to the longitudinal direction, is less than 1 mm over a length in the longitudinal direction corresponding to three consecutive hills.

In certain embodiments, the edges have a portion of rounded shape when viewed in cross-section to the longitudinal direction.

In certain embodiments, the maximum distance between hills and valleys, in a direction transverse to the longitudinal direction and over a length in the longitudinal direction corresponding to three consecutive hills, is comprised between 0.001 mm and 1 mm, more particularly between 0.001 mm and 0.5 mm, even more particularly between 0.001 mm and 0.1 mm.

In certain embodiments, the three consecutive hills are less than a distance corresponding to 15 steps of protruding elements, preferably less than a distance of 25 mm.

In certain embodiments, the width of the base is greater than or equal to 1 mm, preferably greater than or equal to 3 mm, even more preferably greater than or equal to 5 mm and less than or equal to 500 mm, preferably less than or equal to 250 mm, even more preferably less than or equal to 100 mm.

In certain embodiments, the stem of the protruding elements is rotationally symmetrical about an axis perpendicular to the upper surface of the base.

In certain embodiments, the protruding elements have an asymmetrical geometry in relation to a direction transverse to the longitudinal direction of the base.

In certain embodiments, the protruding elements are symmetrical with respect to a plane extending in a longitudinal direction of the base and passing through the axis of the stem of the protruding elements.

In certain embodiments, the support layer consists of a first nonwoven web and a second nonwoven web.

In certain embodiments, the first and second nonwoven webs are of the same nature.

In certain embodiments, the first and second nonwoven webs are different in nature.

In certain embodiments, the first and second nonwoven webs each include non-activated zones 3 and zones activated prior to assembly.

The anti-slip strip may be bonded and/or ultrasonically welded to the upper face of the support layer. The anti-slip strip may also be joined by direct lamination of the anti-slip strip prior to complete solidification of the base of the anti-slip strip so as to cause the support layer to penetrate at least partially into the base.

In the case where the support layer is a set of thermally consolidated fibers and/or filaments, the bond with the base is also achieved by penetration into the base of some of the fibers and/or filaments of the support layer.

If the support layer is a nonwoven web, the protruding elements may be easily removed from the mold even with a nonwoven with a weight of less than 80 g/m$^2$ (mass of material in grams per square meter of nonwoven). For example, the weight of the nonwoven may be comprised between 5 g/m$^2$ and 120 g/m$^2$, or between 25 g/m$^2$ and 100 g/m$^2$, or between 10 g/m$^2$ and 70 g/m$^2$.

This method of joining a support layer to a base including protruding elements is particularly advantageous in that it does not cause deformation of the base, and therefore advantageously makes it possible to preserve the shape of the base obtained during the injection step, and in particular to preserve the straight edges obtainable by the process and apparatus described below.

The present disclosure also relates to an absorbent article, in particular a disposable diaper, including a laminated assembly as defined above.

In certain embodiments, the anti-slip strip of the laminated assembly is arranged on an elastic ear of the absorbent article and/or on a non-elastic ear of the absorbent article, the non-elastic ear including, for example, a nonwoven fabric.

In certain embodiments, the anti-slip strip of the laminated assembly is arranged on an elastic portion of the absorbent article, such as the elastic ear, such that the protruding elements of the anti-slip strip extend towards an absorbent part of the absorbent article.

In certain embodiments, the anti-slip strip of the laminated assembly is arranged on a non-elastic portion of the absorbent article, for example the non-elastic ear, in such a way that the protruding elements of the anti-slip strip extend away from an absorbent part of the absorbent article.

The present disclosure also covers a process for manufacturing a laminated assembly, the process including the following steps:
- forming an anti-slip strip including a base and a plurality of protruding elements extending from the base by distributing an elastomeric material in a molding device;
- assembling a support layer and the anti-slip strip by laminating the support layer and the anti-slip strip.

The direction MD refers to the machine direction and means the direction of travel of the support layer in the machine during the manufacture of the laminated assembly, and the direction CD refers to the cross direction and means the direction perpendicular to the direction MD.

In certain embodiments, the molding device may include a molding strip with a thickness comprised between 100 and 500 μm (micrometers).

In certain embodiments, the assembly of the support layer and the anti-slip strip is carried out before the base of the anti-slip strip is completely solidified so that the support layer penetrates at least partially into the base.

In certain embodiments, the support layer may include a nonwoven web and the distribution of the elastomeric material in the molding device is achieved through the nonwoven web.

In certain embodiments, the assembly of the support layer and the anti-slip strip is carried out by gluing.

In certain embodiments, the assembly of the support layer and the anti-slip strip is carried out by ultrasonic welding.

In certain embodiments, the support layer may include an elastic film, the elastic film being formed by distributing an elastomeric material in the molding device.

In certain embodiments, the support layer may include an elastic film and at least one nonwoven fabric, the anti-slip strip being joined to the support layer by the at least one nonwoven fabric layer.

In certain embodiments, the support layer may include a nonwoven web and an elastic film, the elastic film being produced by distributing an elastomeric material in the molding device and the assembly of the nonwoven web is carried out before complete solidification of the elastic film so as to cause the nonwoven web to penetrate at least partially into the elastic film.

In certain embodiments, the elastomeric material of the elastic film is distributed in the molding device after the elastomeric material of the anti-slip strip has been distributed.

In certain embodiments, the anti-slip strip and the elastic film are made of the same elastomeric material.

In certain embodiments, the support layer may include a second nonwoven web, the assembly of the second nonwoven web being carried out before complete solidification of the elastic film so as to cause the second nonwoven web to penetrate at least partially into the elastic film.

In certain embodiments, the support layer may include a second nonwoven web, the assembly of the second nonwoven web being effected by bonding and/or ultrasonic welding of the second nonwoven web to the elastic film.

In certain embodiments, the molding device may include a molding strip and rotating drive means, the anti-slip strip being formed on the molding strip.

In certain embodiments, the molding device may include a device for forming the heads of the protruding elements including a drive roller and a forming roller.

In certain embodiments, the drive roller and the forming roller rotate at different speeds, so that the heads of the protruding elements are asymmetrical.

In certain embodiments, a ratio of the speed of the drive roller to the speed of the forming roller is greater than or equal to 0.4, preferably greater than or equal to 0.65 and less than or equal to 1.6, preferably less than or equal to 1.35.

In certain embodiments, a ratio of the speed of the drive roller to the speed of the forming roller is greater than or equal to 0.4, preferably greater than or equal to 0.65 and strictly less than 1.

In certain embodiments, a ratio of the speed of the drive roller to the speed of the forming roller is equal to 1.

In certain embodiments, the drive roller and the forming roller rotate at equal speeds, so that the heads of the protruding elements are symmetrical and flat.

BRIEF DESCRIPTION OF THE DRAWINGS

Further features and advantages of the subject matter of the present disclosure will become apparent from the following description of embodiments, given by way of non-limiting examples, with reference to the appended figures, wherein.

In all the figures, the elements in common are identified by identical numerical reference marks.

DETAILED DESCRIPTION

Figure 1:
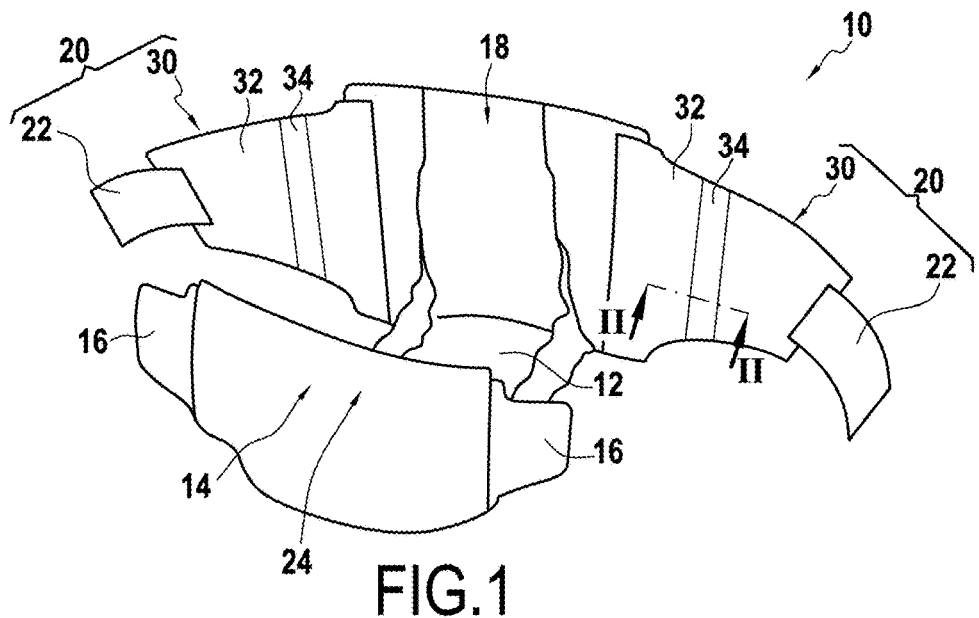
FIG. 1 is a schematic view of a diaper.

FIG. 1 is a highly schematic representation of a diaper 10, for example a disposable diaper. The diaper 10 consists of an absorbent central portion 12 and a front waistband 14 with two front ears 16 and a back waistband 18 with two back ears 20 for attaching the diaper 10 to the diaper's wearer. Each back ear 20 is generally provided with an retaining device 22, for example with hooks, which cooperates with a application zone 24 arranged on the front waistband 14. In the hygiene field, this application zone 24 is commonly referred to as the "landing zone" or in French to the "bande confort".

Figure 2A:
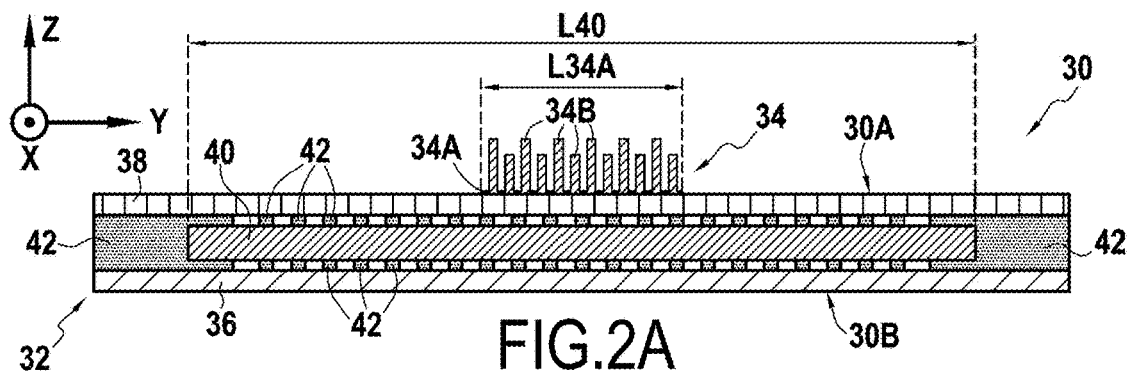
FIG. 2A is a schematic cross-sectional view, according to the plane II-II of FIG. 1, of a laminated assembly according to a first embodiment.

FIG. 2A shows a first embodiment of a laminated assembly 30 that may be used to make a front ear 16 and/or back ear 20 for a diaper 10.

Hereinafter the term laminated assembly will refer to both the uncut laminated assembly and the laminated assembly cut to form the front ear 16 and/or back ear 20 of a diaper 10.

The laminated assembly 30 is shown in FIG. 2A in a cross-sectional view according to the sectional plane II-II of FIG. 1.

The laminated assembly 30 extends in a longitudinal direction X and a lateral direction Y, orthogonal to the longitudinal direction X. The cross-sectional view of FIG. 2A is in the sectional plane YZ, the transverse direction Z being orthogonal to the plane XY and defining the thickness direction of the laminated assembly 30. The directions XYZ are orthogonal to each other.

The laminated assembly 30 in FIG. 2A consists of a support layer 32 and an anti-slip strip 34. The support layer 32 and the anti-slip strip 34 extend in the longitudinal direction X and the lateral direction Y. The laminated assembly 30 consists of an upper face 30A and a lower face 30B.

In the embodiment shown in FIG. 2A, the support layer 32 consists of a first nonwoven web 36, a second nonwoven web 38 and an elastic film 40, joined together with the adhesive 42. The elastic film 40 is joined between the first nonwoven web 36 and the second nonwoven web 38 by laminating the first and second nonwoven webs 36, 38, the elastic film 40 and the adhesive 42.

Figure 6:
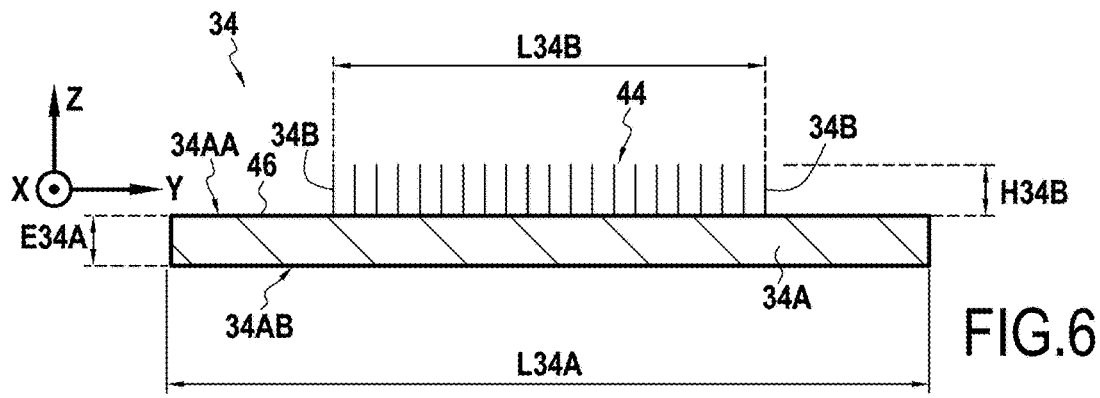
FIG. 6 is a schematic cross-sectional view of an anti-slip strip.

As shown in FIG. 6, the anti-slip strip 34 includes a base 34A and a plurality of protruding elements 34B. The base 34A has an upper face 34AA and a lower face 34AB and the protruding elements 34B extend from the base 34A, in particular from the upper face 34AA of the base 34A. In the lateral direction Y, the base 34A has a width L34A and the protruding elements 34B have a width L34B. The width L34B of the protruding elements 34B is measured in the lateral direction Y between two lines parallel to the longitudinal direction X and to the edges of the base 34A and which include all the protruding elements 34B being tangential to the protruding elements 34B. In the embodiment of FIG. 6, the width L34A of the base 34A is greater than the width L34B of the projecting elements 34B, i.e. the width L34B of the projecting elements 34B is less than or equal to the width L34A of the base 34A.

The protruding elements 34B protrude from the upper face 30A of the laminated assembly 30.

The protruding elements 34B may form an anti-slip strip pattern 44 on the anti-slip strip 34, i.e. the base 34A, in particular the upper face 34AA of the base 34A, may have zones 46 with no protruding elements 34B and a zone of the anti-slip strip 34 with protruding elements 34B forming the anti-slip strip pattern 44. The anti-slip strip pattern 44 may be single or may be repeated several times on the anti-slip strip 34 in the longitudinal direction X and/or the lateral direction Y. The anti-slip strip pattern 44 may include a closed contour.

The base 34A has a thickness E34A in the transverse direction Z and the protruding elements 34B have a height H34B in the transverse direction Z. The height H34B of a protruding element 34B is measured perpendicularly to the upper face 34AA of the base, between the base and a point of the protruding element 34B furthest from the upper face 34AA of the base 34A.

The plurality of protruding elements 34B may include protruding elements 34B having different heights H34B and/or different widths L34BB measured in a plane parallel to the plane XY. The width L34BB is measured at the location of the projecting element having a maximum width.

The protruding elements 34B may be pins and/or studs and/or stems, each stem having a head arranged at an end of the stem opposite the base 34A. The protruding elements 34B may be of a single type for a given anti-slip strip 30 or may be a mixture of one or more types of protruding elements 34B.

Figure 7:
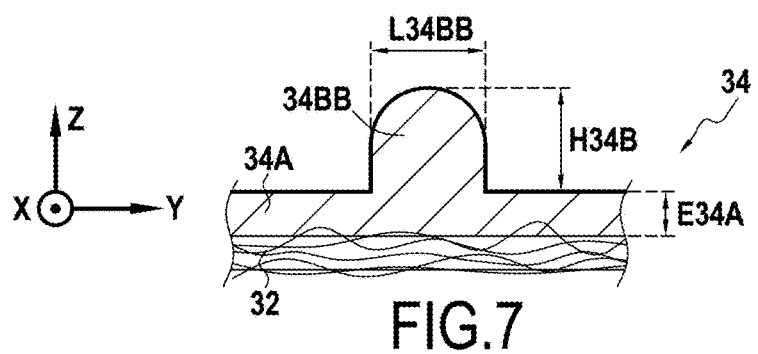
FIG. 7 is a partial schematic cross-sectional view of a laminated assembly according to another embodiment.

As shown in FIG. 7, the anti-slip strip 34 includes pins 34BB having a height H34B in the transverse direction Z and a width L34BB in a plane parallel to the plane XY. In FIG. 7, only one pin 34BB has been shown. The pin 34BB has a height H34B greater than or equal to the width L34BB. When the height H34B is less than the width L34BB, it is referred to as a pin. The anti-slip strip 34 is laminated with a support layer 32, formed in this embodiment by a nonwoven web, part of the fibers of which have penetrated the base 34A of the anti-slip strip. It is therefore understood that the assembly of the support layer 32 and of the anti-slip strip 34 has been carried out before complete solidification of the base 34A of the anti-slip strip 34 so as to cause the support layer 32 to penetrate at least partially into the base 34A. As shown in FIG. 7, an anti-slip strip 34 and a support layer 32 including a nonwoven are shown. This nonwoven may form a front ear 16 and/or a back ear 20 for a diaper 10, in particular the anti-slip strip 34 may be arranged on the front ear 16 in such a way that the protruding elements extend towards the absorbent part of the absorbent article and/or extend away from the absorbent part of the absorbent article.

Protruding elements including a stem surmounted by a head are shown in FIGS. 20 to 23.

Figure 2B:
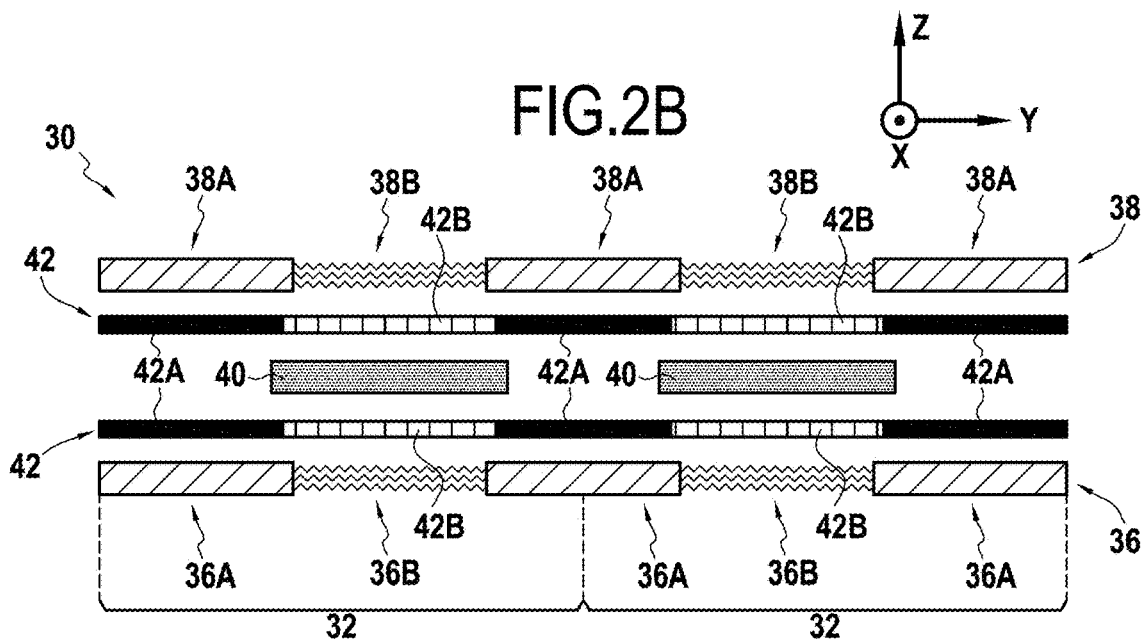
FIG. 2B is an exploded schematic cross-sectional view of a support layer.

FIG. 2B is an exploded view of two support layers 32 according to FIG. 2A and shows a possible way of joining the support layer 32. In FIG. 2B, two support layers 32 are shown joined together. In order to form the support layer 32, after the nonwoven webs, the elastic film and the adhesive films have been laminated together, the entire FIG. 2B is cut in the middle to form two support layers 32.

In the embodiment shown in FIG. 2B, the support layer 32 consists of a first nonwoven web 36 and a second nonwoven web 38. The first and second nonwoven webs 36, 38 may be of the same or different nature.

In the embodiment of FIG. 2B, the first and second nonwoven webs 36, 38, each include non-activated zones 36A, 38A and activated zones 36B, 38B prior to assembly.

In the embodiment of FIG. 2B, the dimension in the lateral direction Y of the activated zones 36B, 38B are equal. They could be different from one web to another and/or within the same web. The first and second nonwoven webs 36, 38 may also have no activated zones, as the activation of the support layer is achieved after bonding with the elastic film 40.

The adhesive 42 is applied to the first and second nonwoven webs 36, 38. The adhesive 42 is arranged in solid strips 42A and in thin lines 42B. The adhesive 42 thus forms a plurality of lines of adhesive 42B, for example continuous in longitudinal direction X. The elastic film 40 has a width L40. The width L34A of the base 34A of the anti-slip strip 34 is less than the width L40 of the elastic film 40. In the example in FIG. 2A, the width L34A of the base 34A of the anti-slip strip 34 corresponds to 25% of the width L40 of the elastic film 40.

The anti-slip strip 34 may be bonded and/or ultrasonically welded to the upper face 30A of the support layer 32. The anti-slip strip 34 may also be joined by laminating the anti-slip strip 34 prior to complete solidification of the base 34A of the anti-slip strip 34 so as to cause the support layer 32 to penetrate at least partially into the base 34A, in the manner shown in FIG. 2A, the second nonwoven web 38.

Figure 20:
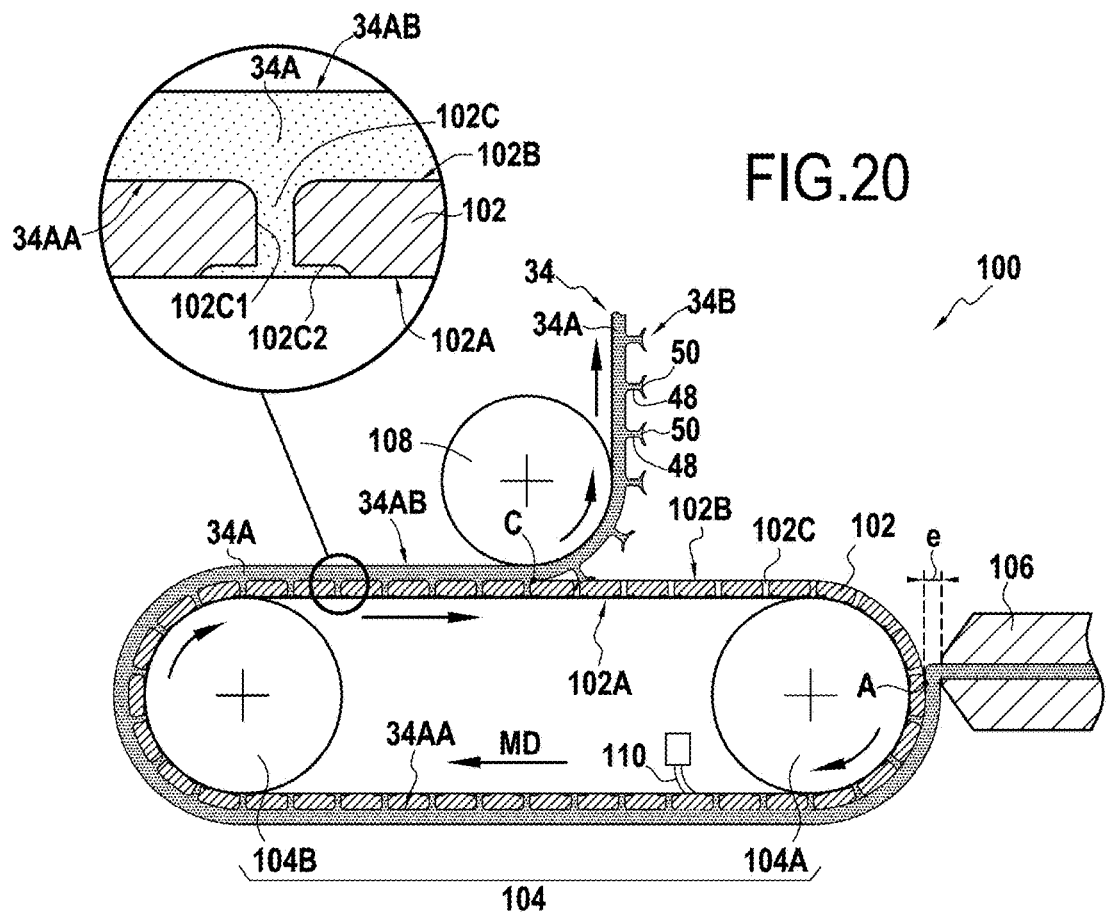
FIG. 20 is a schematic representation of an example of an apparatus for producing an anti-slip strip.

The anti-slip strip 34 may be manufactured, for example, using an apparatus 100 as shown in FIG. 20. The apparatus 100 allows the manufacture of an anti-slip strip 34 for a laminated assembly 30. The anti-slip strip 34 includes the continuous base 34A and the plurality of protruding elements 34B. In the embodiment of FIG. 20, each protruding element 34B includes a stem 48 surmounted by a head 50. The head 50 is arranged at an end of the protruding element 34B opposite the base 34A, in particular at the upper face 34AA of the base 34A.

The apparatus 100 as shown includes a molding strip 102 positioned on rotary drive means 104 including two rollers 104A, 104B, a material distribution means 106, for example an injector, adapted to carry out an injection of elastomeric molding material.

The assembly formed by the molding strip 102 and the rotary drive means 104 thus forms a molding device.

The illustrated example including two rollers 104A, 104B is not exhaustive, the number and arrangement of the roller(s) may vary in particular to adapt to the length of the molding strip 102 and the different stations of the apparatus. For example, three rollers could be used, or even a single roller so that the molding strip is arranged on the periphery of the single roller, such molding strip forming a sleeve. In particular, only one of the two rollers may be driven in rotation by motorized means, for example the roller 104A, the other roller 104B being free, i.e. without motorized means, and driven in rotation via the molding strip, itself driven by the roller 104A. The direction of travel of the molding strip defines the direction MD of the anti-slip strip.

The molding strip 102 as shown includes an inner face 102A and an outer face 102B, the inner face 102A being in contact with the rotary drive means 104.

The material distribution means 106 is arranged so as to inject molding material onto the outer face 102B of the molding strip 102.

Specifically, the material distribution means 106 is arranged opposite the molding strip 102, spaced from the molding strip 102 so as to define an air gap e shown in FIG. 20, wherein the boundary of the material injected onto the outer face 102B of the molding strip 102 is marked by the reference A, corresponding to the trailing edge of the material injected onto the molding strip 102 with respect to the direction of travel of the molding strip 102.

The molding strip 102 is provided with a plurality of cavities 102C allowing the realization of the protruding elements 34B of the anti-slip strip 34.

The cavities 102C are each formed so as to define a stem 102C1 extending from the outer face 102B to the inner face 102A of the molding strip 102 and a head 102C2 extending between the stem 102C1 and the inner face 102A of the molding strip 102.

In the example shown, the heads 50 of the cavities 102C open onto the inner face 102A of the molding strip 102. The cavities 102C are therefore through-going. The cavities 102C may also be blind, i.e. they do not open out from the inner face 102A of the molding strip 102, and/or cavities 102C may have only one stud or pin.

The portions of the cavities 102C forming the stems 102C1 typically extend in a direction perpendicular to the outer face 102B of the molding strip 102. The portions of the cavities 102C forming the stems 102C1 typically have a rotational geometry about an axis perpendicular to the outer face 102B of the molding strip 102, or a geometry having a plane of symmetry extending in a direction parallel to the direction of travel of the molding strip 102 and/or in a direction perpendicular to the direction of travel of the molding strip 102.

The portions of the cavities 102C forming the heads 102C2 typically extend radially or transversely with respect to an axis perpendicular to the outer face 102B of the molding strip 102, and may be rotationally symmetrical about this axis perpendicular to the outer face 102B of the molding strip 102. The portions of the cavities 102C forming the heads 102C2 typically have a substantially frustoconical or hexahedral shape.

The portions of the cavities 102C forming the heads 102C2 may be linear or curved, for example to form curved portions towards the inner face 102A or towards the outer face 102B of the molding strip 102 extending from the portions of the cavities 102C forming the stems 102C1.

The portions of the cavities 102C forming the heads 102C2 may have a constant or variable thickness.

In the example shown in the figures, the portions of the cavities 102C forming the heads 102C2 extend radially around the portions of the cavities 102C forming the stems 102C1, and are generally disc-shaped.

The molding strip 102 may have on its inner face 102A or on its outer face 102B a particular texture such as grooves, groove pattern or vent or pin pattern, or be substantially smooth, for example as described in application WO2017187103, incorporated by reference.

The molding strip 102 may be formed by superimposing several strips, and is therefore not necessarily a single piece or material.

The material distribution means 106 is typically arranged so as to carry out the injection of molding material into the molding strip 102 at a section of the molding strip 102 where the latter is supported against a drive roller, in this case the drive roller 104A in the example shown in FIGS. 20 and/or 21. The drive roller then forms a bottom for the cavities 102C.

In the case where the injection of molding material is carried out while the molding strip 102 is not supported against a drive roller, the material distribution means 106 may then include a base disposed on the other side of the molding strip 102, so that the inner face 102A of the molding strip 102 is supported against the base when the injection of material is carried out, the base then forming a bottom for the cavities 102C of the molding strip 102.

The use of a molding strip 102 in combination with drive means 104 compared with the use of conventional forming means such as rollers in which molding cavities are directly formed is advantageous for several reasons.

The use of a molding strip 102 is of particular interest in terms of modularity. The molding strip may in fact be easily removed and replaced from the drive means, unlike a massive roller for which disassembly and reassembly operations are particularly complex to carry out. Such an advantage is particularly noticeable when the two rollers 104A, 104B are fixed to a frame on the same side, leaving the end of the other side free to introduce/remove the molding strip. A means of guiding the molding strip may also be used to facilitate the insertion and/or removal of the molding strip. A guide means may include a tensioning element for the molding strip.

Moreover, the production of a molding strip is greatly simplified compared with the production of a roller with molding cavities. Such rollers are in fact typically made by stacking successive slices, thus requiring multiple machining operations and leading to significant constraints during assembly and at each change of reference of protruding elements, and have a large mass requiring the holding of these rollers by their two ends, which consequently complicates their replacement.

The cavities 102C in the molding strip 102 may be produced by an etching process or by using a laser where it is desired to form protruding elements 34B. It may also be envisaged to produce the molding strip 102 with cavities 102C distributed evenly over the entire molding strip 102 and then fill in the cavities 102C where it is desired to form zones 20 without projections 34B. A molding strip made of for example nickel or stainless steel or non stainless steel could be used.

The separation between the anti-slip strip 34 and the molding strip 102 is marked in FIG. 20 by the reference C, for example the point at which the base 34A of the anti-slip strip 34 is no longer in contact with the molding strip 102. It may be provided that the molding strip 102 is loaded onto the release roller 108, i.e. the release roller 106 forms a lever in the molding strip 102 to facilitate the release of the protruding elements from the mold.

In the example shown, the cavities 102C of the molding strip 102 are through-going. The apparatus may then include an element, such as a doctor blade 110, positioned to scrape the inner face 102A of the molding strip 102 to remove excess molding material if necessary. Injection means the action of shaping a molten molding material, for example, dispensing, feeding, molding, injecting, extruding.

The anti-slip strip 34 may thus be formed by distributing the elastomeric material by the material distribution means 106 into the cavities 102C of the molding strip 102 and against the outer face 102B of the molding strip 102. The molding strip 102 of FIG. 20 has cavities 102C, each cavity being formed to define a stem 102C1 extending from the outer face 102B to the inner face 102A of the molding strip 102 and a head 102C2 extending between the stem 102C1 and the inner face 102A of the molding strip 102. The molding strip 102 may include cavities 102 having no portion for defining a head 102C2. The cavities 102C of the molding strip 102 may also be non-through cavities and therefore not open to the inner face 102A of the molding strip 102.

Figure 28:
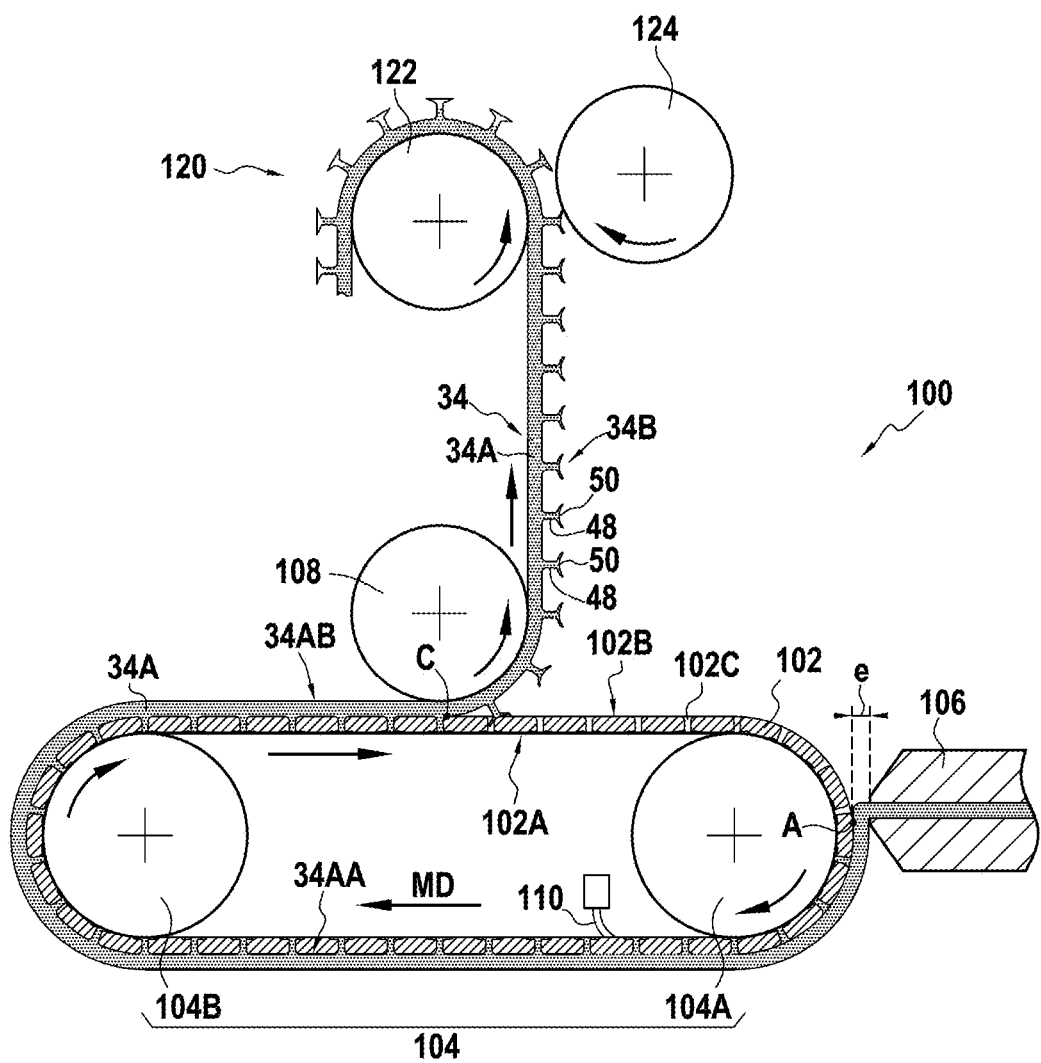
FIG. 28 is a schematic representation of an example of an apparatus for producing an anti-slip strip including a forming device.

Protruding elements including a stem surmounted by a head are shown in FIG. 28. These protruding elements are obtained by calendering the protruding elements shown in FIGS. 20 to 23 with a forming device 120 including a drive roller 122 and a forming roller 124.

When symmetrical and flat heads 50 are desired, the speeds of the drive roller 122 and forming roller 124 are identical.

When asymmetrical heads 50 are to be formed, the speeds of drive roller 122 and forming roller 124 are different. In particular, the following ratio $V122/V124=A$ may be used, with A greater than or equal to 0.4, preferably greater than or equal to 0.65 and less than or equal to 1.6, preferably less than or equal to 1.35.

Figure 8:
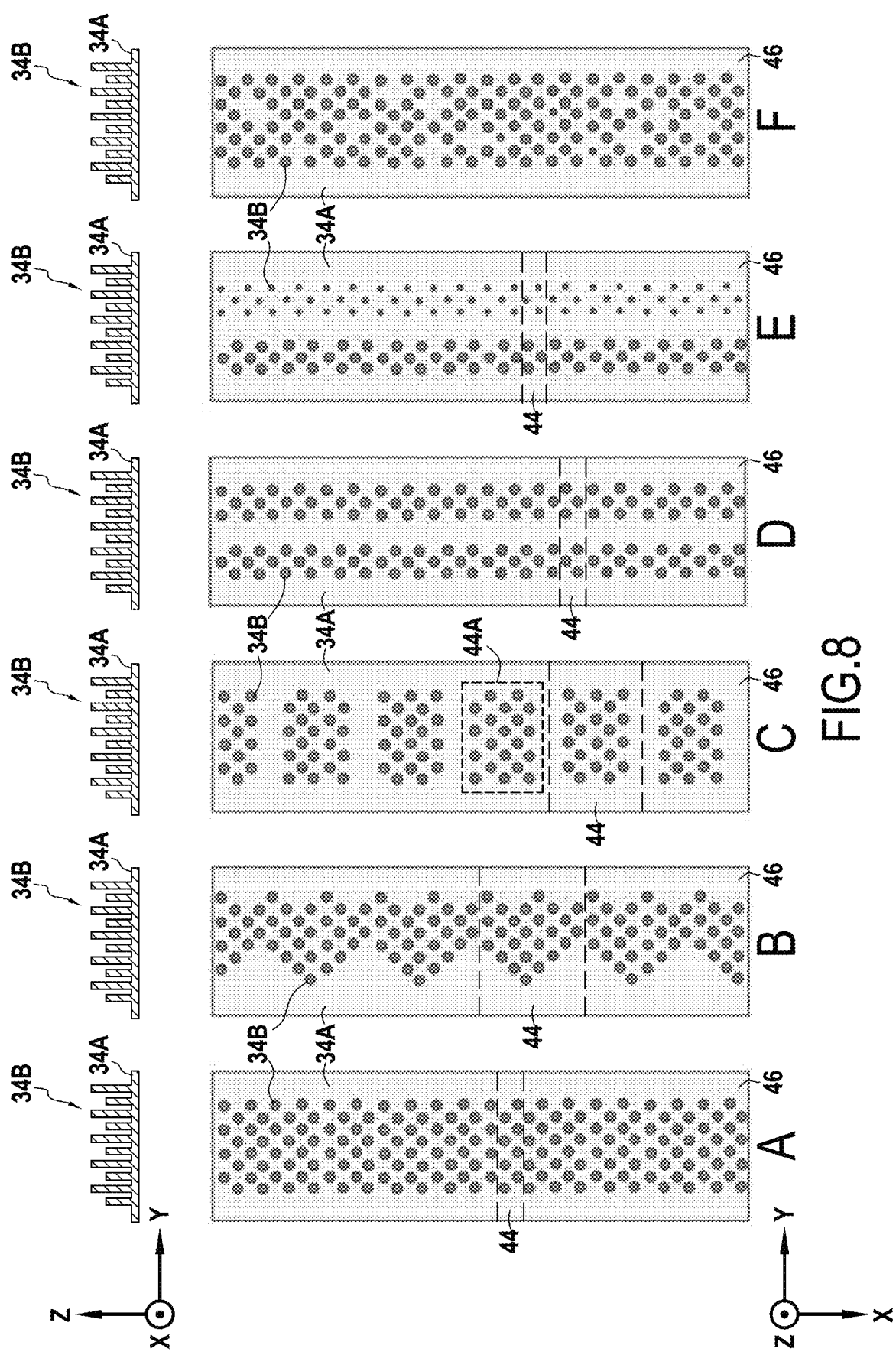
FIGS. 8A-8F are schematic cross-sectional and top views of the different embodiments of the anti-slip strip.

Examples of the anti-slip strip 34 are shown in FIGS. 8A-8F. As can be seen, not all protrusions 34B have a uniform height H34B and may have different widths L34BB (see in particular the embodiment of FIG. 8E). It can also be seen that the projecting elements 34B generally form an anti-slip strip pattern 44 which is repeated in the longitudinal direction X (see FIGS. 8A-8F). The anti-slip strip pattern extends over the entire width L34A of the base 34A of the anti-slip strip 34, i.e. the dimension of the anti-slip strip in the lateral direction Y or the direction CD. However, the anti-slip strip 34 may also have no repeating pattern and be formed of a single anti-slip strip pattern, as shown in FIG. 8F. The protruding elements 34B may form an anti-slip strip pattern 44 with a closed contour 44A. The protruding elements 34B may have a different density in the longitudinal direction X and the lateral direction Y and/or along the longitudinal direction X and/or the lateral direction Y.

The support layer 32 may then be joined with the anti-slip strip 34 by means of adhesive, ultrasonic welding, and/or by melting the base 34A or support layer 32.

The apparatus presented above and the associated process may also have means and a step for assembling a support layer 32 to the base 34A.

In order to carry out the assembly of the support layer 32 to the base 34A of the anti-slip strip 34, the proposed apparatus 100 may include means for driving the support layer 32, adapted to carry out a tape feed and to apply the support layer 32 against the underside 34AB of the base 12 downstream of the material distribution means 106.

Figure 21:
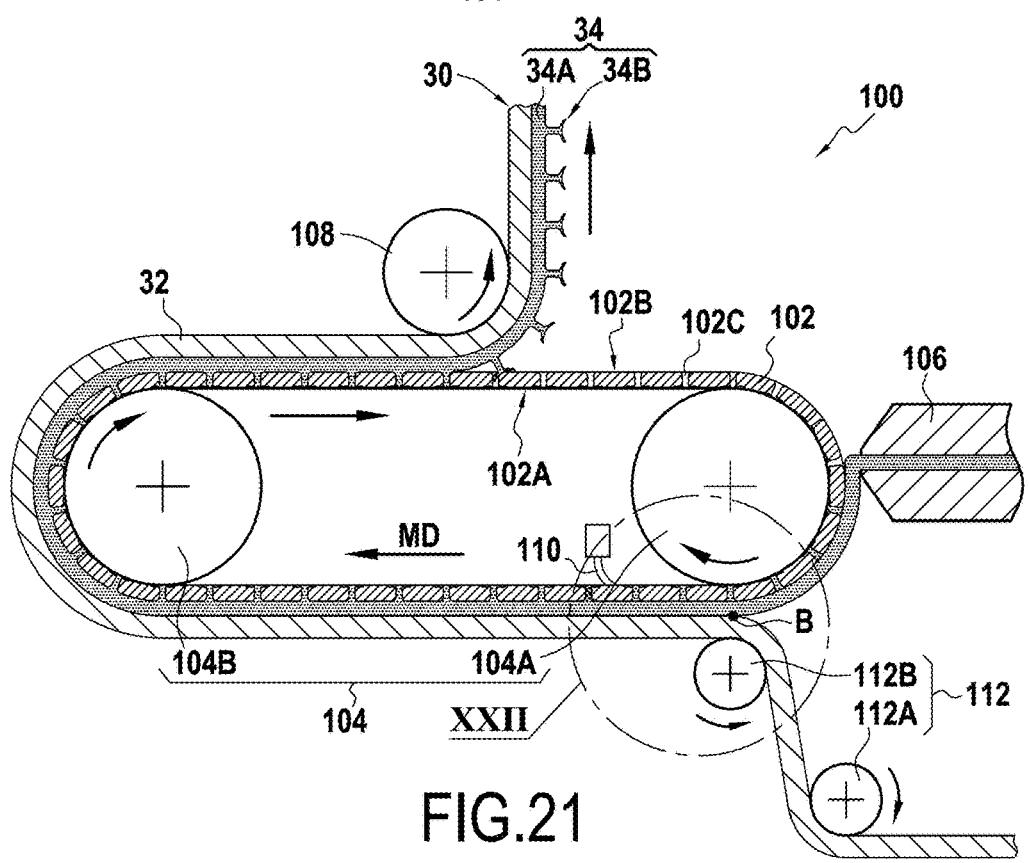
FIGS. 21 to 23 are schematic representations of examples of apparatus for producing a laminated assembly.
Figure 22:
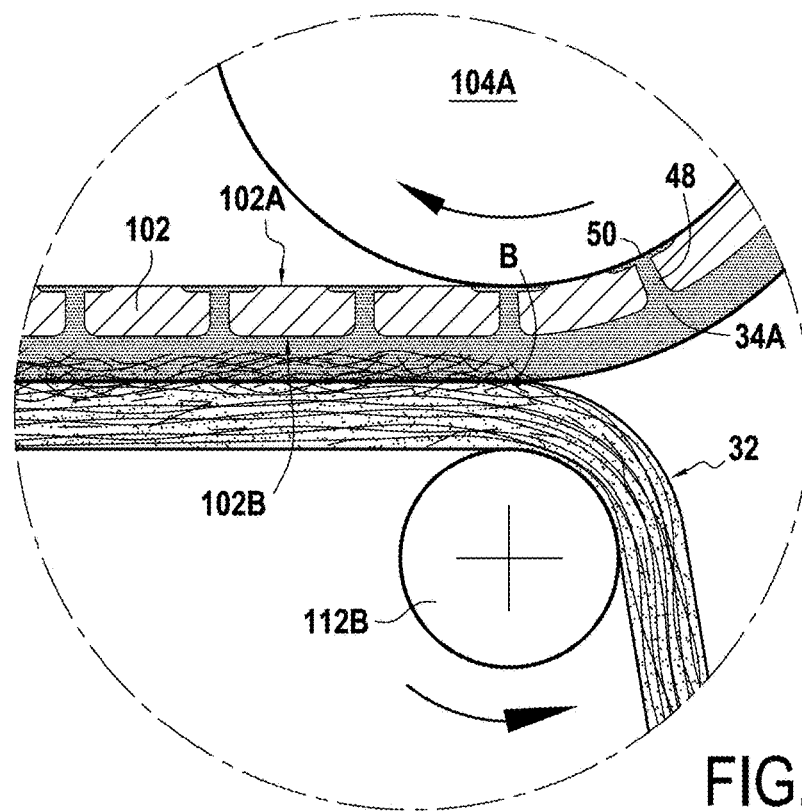

FIGS. 21 and 22 schematically show an example of apparatus 100 including such means. FIG. 22 is a detailed view of the zone XXII of FIG. 21.

The apparatus as illustrated is similar to that previously shown with reference to FIG. 20; the common elements are therefore not described again here.

As can be seen in FIGS. 20 and 21, the apparatus as shown includes web drive means 112, here consisting of two rollers 112A, 112B, configured to provide a feed of the support layer 32 downstream of the material distribution means 106. In this embodiment, the direction MD of the anti-slip strip 34 is merged with the direction MD of the support layer 32.

The support layer 32 is typically a layer of nonwoven material, a thermoplastic film, an elastic film or a composite film, or an assembly of thermally consolidated fibers and/or filaments.

In the example shown in FIGS. 20 and 21, the support layer 32 is shown as a nonwoven web.

The drive means 112 of the support layer 32 are configured to feed the support layer 32 to the apparatus, and apply this support layer 32 against the lower face 34AB of the base 34 downstream of the material distribution means 106.

The drive means 112 are configured so that this application is carried out prior to the complete solidification of the base 34A. Thus, this application results in at least partial penetration of the support layer 32 beyond a plane defined by the lower face 34AB of the base 34. The point of contact between the base 34A and the support layer 32 is marked by reference B in the figures.

More precisely, the lower face 34AB of the base 34 is substantially flat, and defines a plane. The application of the support layer 32 against this lower face 34AB causes portions of the support layer 32, for example fibers and/or filaments of the nonwoven web, in the case where the support layer 32 is a nonwoven web, to penetrate into the base 34A, thereby penetrating the lower face 34AB of the base 34A.

Since such application is carried out prior to the complete solidification of the base 34A, it is not necessary to heat the base 34A and/or the support layer 32 in order to achieve such a bond.

By way of example, considering a base 34A made of VISTAMAXX 7050 FLX (available from ExxonMobil Chemical, Houston, Tex.), the application of the substrate against the lower face 34AB of the base 34A is typically performed when the lower face 34AB of the base 34A has a temperature comprised between the melting temperature of the material and the Vicat B softening temperature of the constituent material minus 30° C. or between the melting temperature of the constituent material and the Vicat A softening temperature of the constituent material. More particularly, when the base comprises a polyolefin-based material, the lower face 34AB of the base 34A has a temperature comprised between 150° C. and 200° C., typically of the order of 175° C., this temperature being typically measured by means of an infrared or laser camera. The VICAT softening temperature is defined as the temperature obtained according to one of the methods described in standards ISO 306 or ASTM D1525 with a heating rate of 50° C./h and a standard load of 50 N for VICAT B and a standard load of 10 N for VICAT A.

The support layer 32 may be applied uniformly or non-uniformly against the lower face 34AB of the base 34A.

The bond between the support layer 32 and the base 34A may be uniform or non-uniform.

In the case where the support layer 32 is a thermally consolidated set of fibers and/or filaments, bonding to the base 34A is also achieved by penetration into the base 34A of some of the fibers and/or filaments of the support layer 32.

If the support layer 32 is a nonwoven web, the protruding elements may be easily removed from the mold even with a nonwoven with a weight of less than 80 g/m² (material mass in grams per square meter of nonwoven). By way of example, the weight of the nonwoven may be comprised between 5 g/m² and 120 g/m², or between 25 g/m² and 100 g/m², or between 10 g/m² and 70 g/m².

This method of joining a support layer 32 to a base 34A including protruding elements 34B is particularly advantageous in that it does not cause deformation of the base 34A, and therefore advantageously makes it possible to retain the shape of the base 34A obtained during the injection step, and in particular to retain the straight edges obtainable by the process and apparatus described above.

In the case where the support layer 32 is a nonwoven web, the apparatus may include a calendering device upstream of the drive means 112, thus making it possible to carry out a step of calendering locally or not of the nonwoven web prior to its application against the base 34A.

The apparatus 100 of FIGS. 21 and 22 may be used to laminate the anti-slip strip 34 and the support layer 32, where the support layer 32 may include one or more nonwoven webs with or without thermoplastic film (elastic or non-elastic), such as for example the support layer 32 in FIG. 2A.

The apparatus 100 of FIGS. 21 and 22 may also be used to join the anti-slip strip 34 to the second nonwoven web 38 of FIG. 2A, the second nonwoven web 38 and the anti-slip strip 34 being then joined to the elastic film 40 and the first nonwoven web 36 of FIG. 2A.

Figure 3:
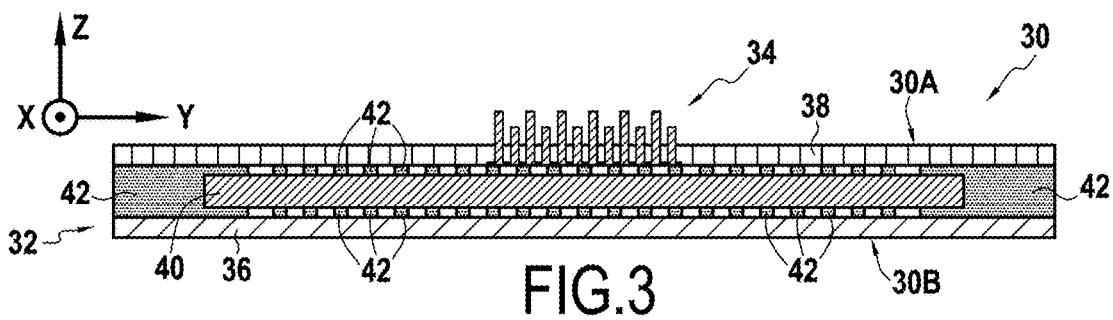
FIGS. 3 to 5 are schematic cross-sectional views of a laminated assembly according to other embodiments.

The embodiment of FIG. 3 differs from the embodiment of FIG. 2A, in particular in that the anti-slip strip 34 passes through the second nonwoven web 38, with the protruding elements 34B projecting from the upper face 30A of the laminated assembly 30.

Figure 23:
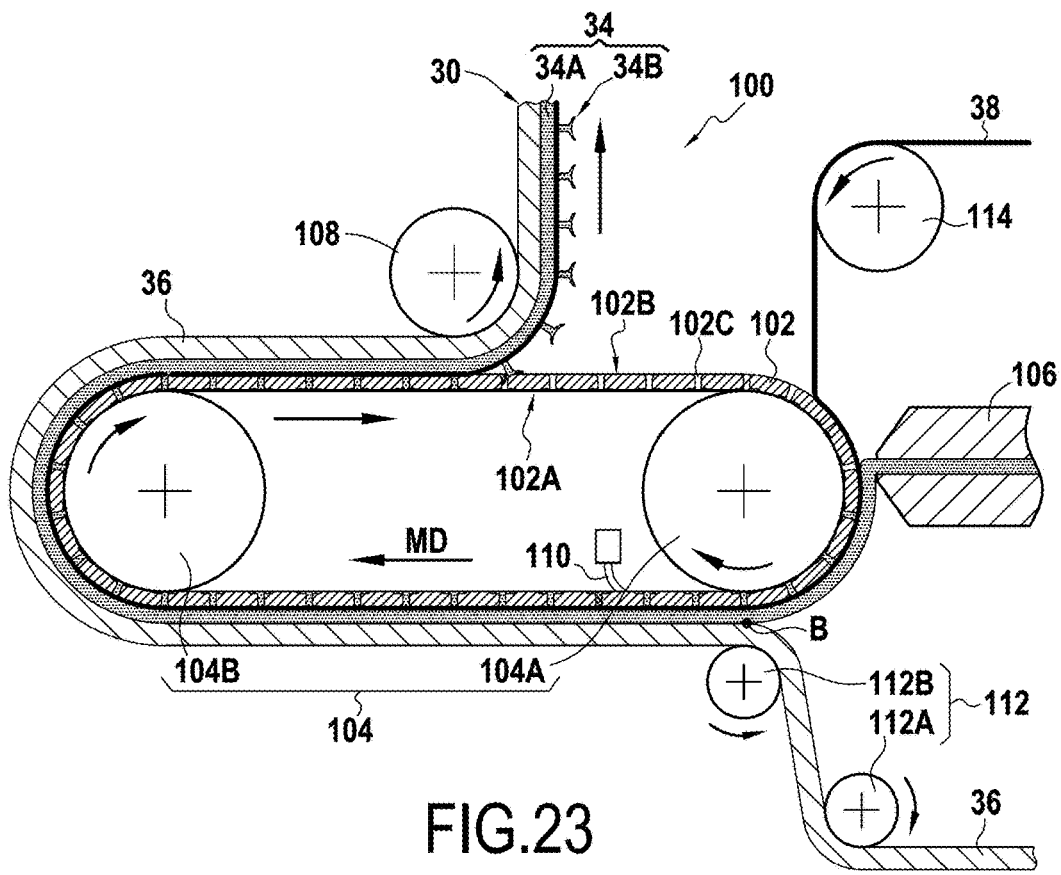

In this embodiment, the anti-slip strip 34 is formed by distributing the elastomeric material in the cavities 102C of the molding strip 102 through the second nonwoven web 38. The apparatus 100 includes, as for the apparatus of FIG. 23, drive means 114 configured to provide a feed of the second nonwoven web 38 upstream of the material distribution means 106. The anti-slip strip 34 being injected through the second nonwoven web 38, causing portions of the second nonwoven web 38 to penetrate into the base 34A. In FIG. 23, for reasons of simplicity, the second nonwoven web 38 has been shown with a lower thickness than the thickness shown for the first nonwoven web 36. The thickness of the first and second nonwoven webs 36, 38 could be similar or different depending on the application.

Since such application is carried out prior to the complete solidification of the base 34A, it is not necessary to heat the base 34A and/or the support layer 32 in order to achieve such a bond.

The second nonwoven web 38 and the anti-slip strip 34 are then joined to the elastic film 40 and the first nonwoven web 36 in FIG. 3. The base material and the elastic film material may be the same or different but still be elastomeric materials.

Figure 4:
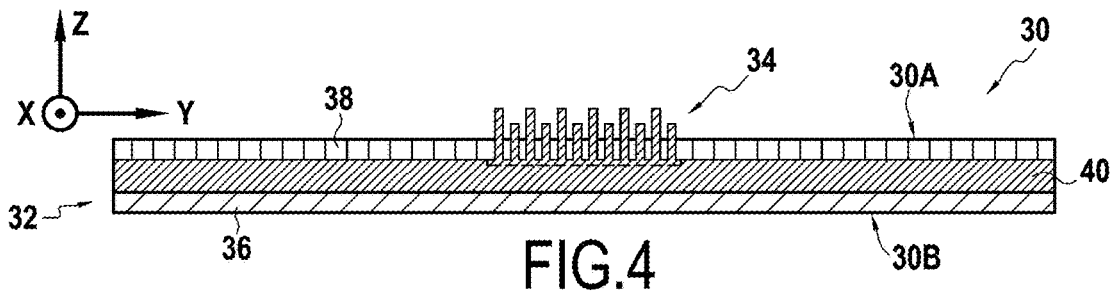

In the embodiment of FIG. 4, the elastic film 40 is made of elastomeric material. The elastomeric material of the elastic film is, for example, the same as the elastomeric material of the anti-slip strip, and the first and second nonwoven webs 36, 38 are laminated to the elastic film 40 without the addition of adhesive.

Typically, the first and second nonwoven webs 36, 38 may be bonded to the elastic film 40 prior to complete solidification of the elastic film 40 by applying the first nonwoven web 38 against the lower face 34AB of the base 34A and the second nonwoven web 36 against the upper face 34AA of the base 34A, causing portions of the first and second nonwoven webs 36, 38 to penetrate into the base 34A.

Since such application is carried out prior to the complete solidification of the base 34A, it is not necessary to heat the base 34A and/or the support layer 32 in order to achieve such a bond. The material of the base and the material of the elastic film may be the same or different but still be elastomeric materials. According to an alternative embodiment not shown, the first nonwoven web could be bonded to the elastic film via an adhesive layer (continuously and/or in the form of adhesive lines, for example as shown in FIG. 3).

The apparatus 100 of FIG. 23 includes drive means 112, 114 respectively configured to provide a feed of the first nonwoven web 36 downstream of the material distribution means 106 and to provide a feed of the second nonwoven web 38 upstream of the material distribution means 106.

When the elastomeric material of the anti-slip strip 34 is different from the elastomeric material of the elastic film 40 or when the film 40 is a non-elastic thermoplastic film, the apparatus of FIG. 23 includes a second material distribution means arranged downstream of the material distribution means 106.

Figure 5:
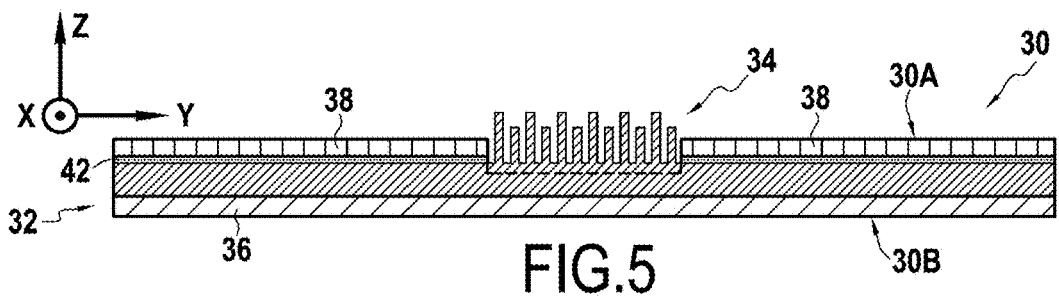

In the embodiment of FIG. 5, the second nonwoven web 38 is assembled by bonding by means of an adhesive 42 to the elastic film 40. The second nonwoven web 38 is in two parts, each part being arranged on either side of the anti-slip strip 34. The base material and the material of the elastic film may be the same or different but still be elastomeric materials. According to an alternative embodiment not shown, the first nonwoven web could be bonded to the elastic film via an adhesive layer (continuously and/or in the form of adhesive lines, for example as shown in FIG. 3).

In the embodiments of FIGS. 2 to 4, the anti-slip strip is arranged in the middle in the lateral direction Y of the support layer 32. In the embodiment of FIG. 5, the anti-slip strip is not centered.

Figure 24A:
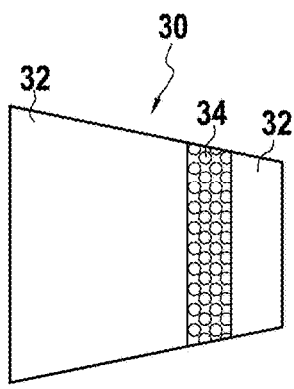
FIGS. 24A-24C are schematic representations of laminated assemblies.
Figure 24B:
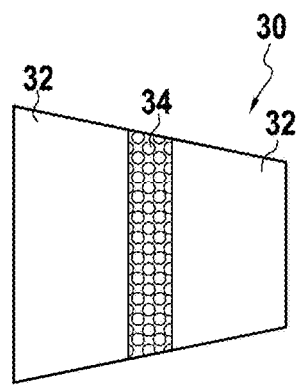
Figure 24C:
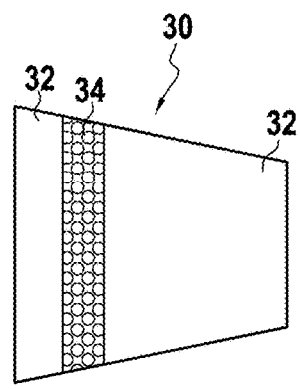

The anti-slip strip 34 may be placed at different positions on the support layer 32 as shown in FIGS. 24A-24B. The anti-slip strip may be placed in any position intermediate between the positions shown in FIGS. 24A-24C. In FIGS. 24A-24C, the anti-slip strip 34 has a dimension in the direction MD which is larger than a dimension in the direction CD, it is understood that the anti-slip strip has a length in the direction MD and a width in the direction CD.

The molding strips 102 of FIGS. 20 to 23 have cavities 102C, each cavity being formed to define a stem 102C1 extending from the outer face 102B to the inner face 102A of the molding strip 102 and a head 102C2 extending between the stem 102C1 and the inner face 102A of the molding strip 102. The molding strip 102 may include cavities 102 having no portion for defining a head 102C2. The cavities 102C of the molding strip 102 may also be non-through cavities and therefore not open to the inner face 102A of the molding strip 102.

FIGS. 9 to 19 show molding strips 102 for forming anti-slip strips 34 with various patterns.

Figure 9:
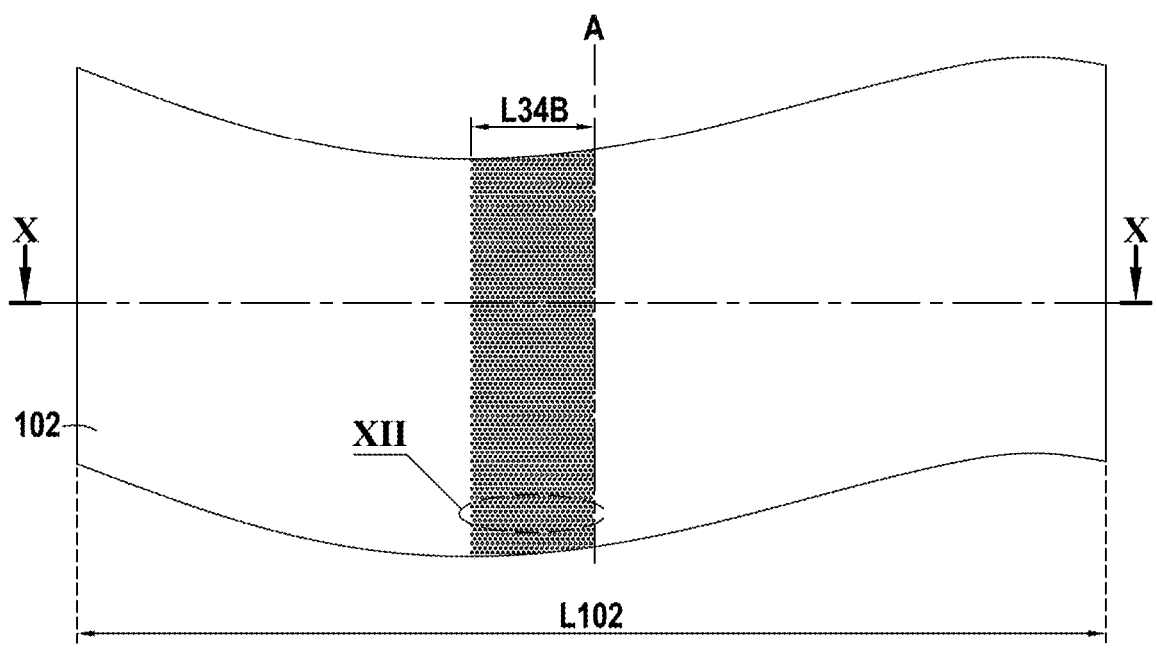
FIG. 9 is a partial schematic view of the top of a molding strip.
Figure 10:
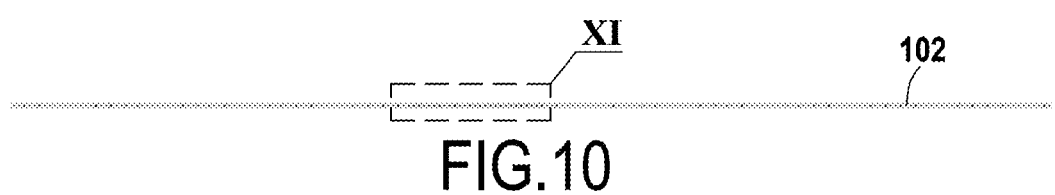
FIGS. 10 and 11 are schematic cross-sectional views of the molding strip in FIG. 9.
Figure 11:
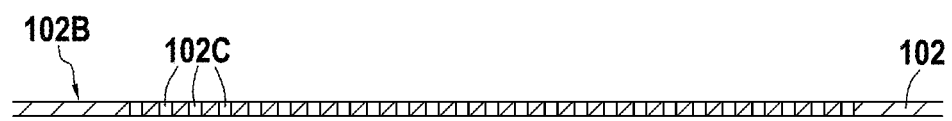
Figure 12:
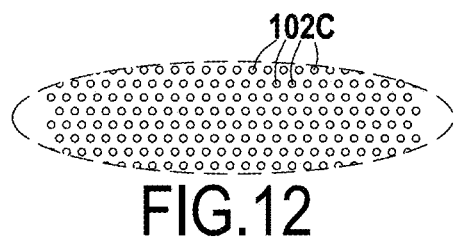
FIG. 12 is an enlarged schematic view of a pattern of a zone XII of the molding strip in FIG. 9.

FIG. 9 is a partial view of a molding strip 102 whose width L102 in the lateral direction Y is greater than the width L34B of the protruding element pattern 34B. The molding strip 102 is seen from the outer face 102B. FIG. 10 is a cross-sectional view according to the sectional plane X-X of FIG. 9 and FIG. 11 is an enlargement XI of FIG. 10 showing the molding cavities 102C of the molding strip 102. FIG. 12 is an enlarged view of FIG. 9 showing the cavities 102C of the molding strip 102. Note that in the embodiment of FIG. 9, the perforated portion of the molding strip 102 is not centered with respect to the axis of symmetry A of the molding strip 102. The perforated part of molding strip 102, corresponding to the width L34B of the protruding elements 34B on the base 34A of the anti-slip strip 34 could be centered on the axis of symmetry A or even offset to the left or right of FIG. 9.

For example, the anti-slip strip 34 obtained by distributing elastomeric material with the molding strip 102 in FIGS. 9 to 12 is an anti-slip strip with a width L34A measured in the lateral direction Y equal to 20 mm. Taking the full width L34A of the anti-slip strip, a zone of 22.52 mm$^2$ comprises 49 protruding elements 34B, i.e. a density of 217.616 protruding elements per cm$^2$, representing 13.40% of the total area of the base 34A.

Figure 13:
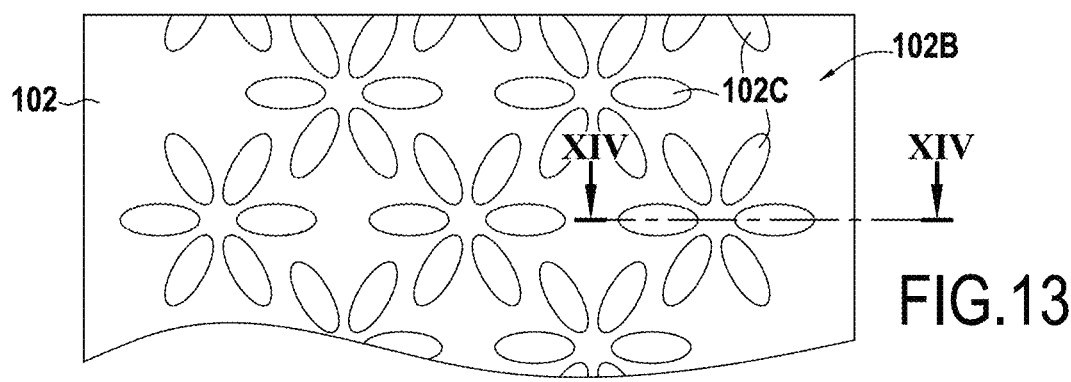
FIG. 13 is a schematic view of a pattern of elements of a molding strip according to another embodiment.
Figure 14:
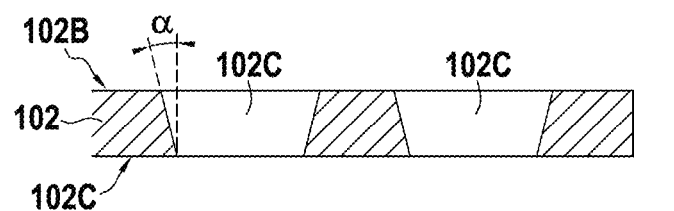
FIG. 14 is a partial schematic cross-sectional view according to the plane XIV-XIV of the molding strip in FIG. 13.

FIG. 13 is a view of molding strip 102 similar to the view in FIG. 12 and FIG. 14 is a cross-sectional view along the plane XIV similar to the view in FIG. 11 for the pattern in FIG. 13. FIG. 13 shows a "flower" pattern of the cavities 102C of the molding strip 102. As shown in FIG. 14, the cavities 102 may have a draft, here an angle α of 10° or less, to facilitate the removal of protruding parts from the mold.

For example, the anti-slip strip 34 obtained by distributing elastomeric material with the molding strip 102 in FIGS. 13 and 14 is an anti-slip strip whose width L34A measured in the lateral direction Y is equal to 20 mm. Taking the full width L34A of the anti-slip strip, a zone of 130 mm$^2$ comprises 30 protruding elements 34B, i.e. a density of 23.077 protruding elements per cm$^2$, representing 29.05% of the total area of the base 34A.

Figure 17:
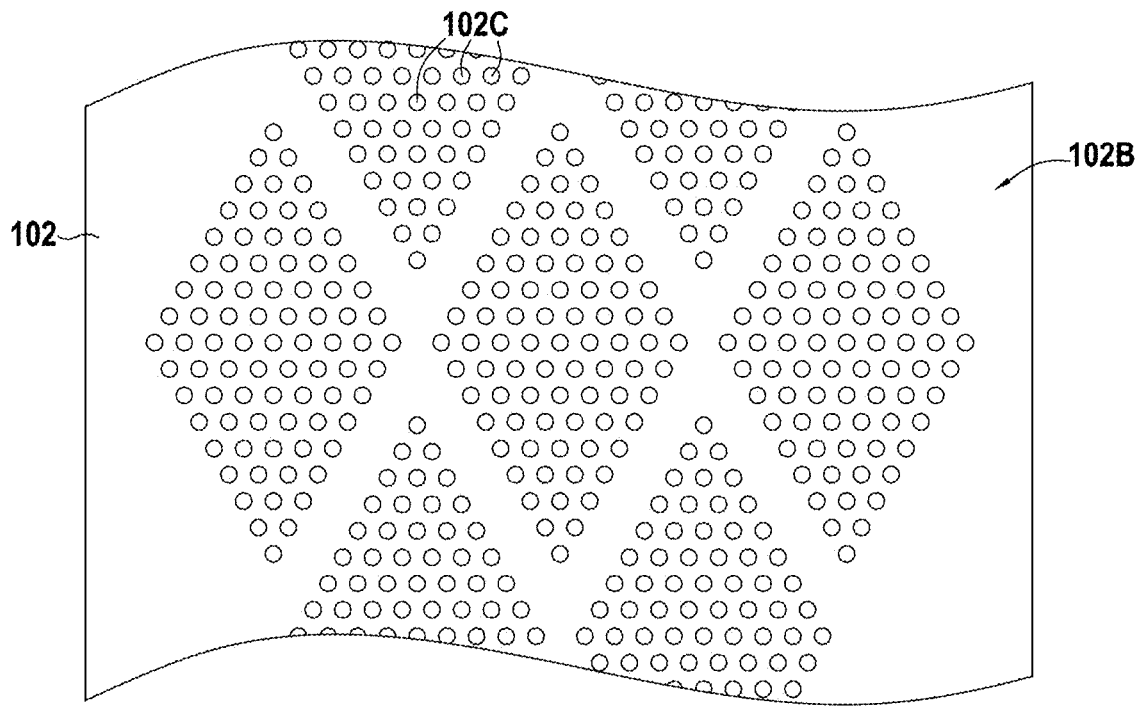
Figure 18:
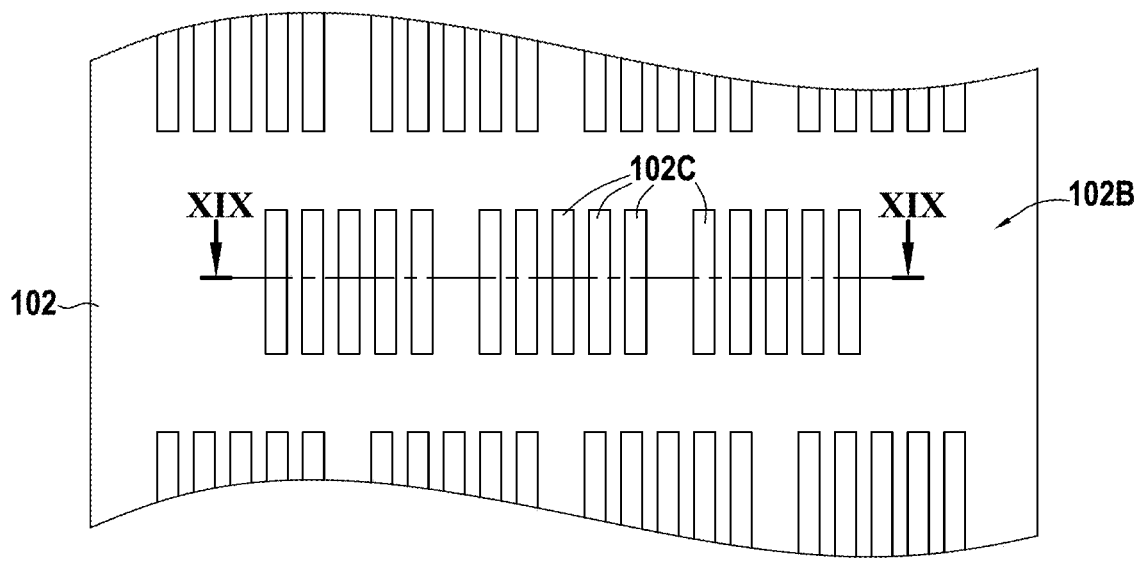
Figure 19:
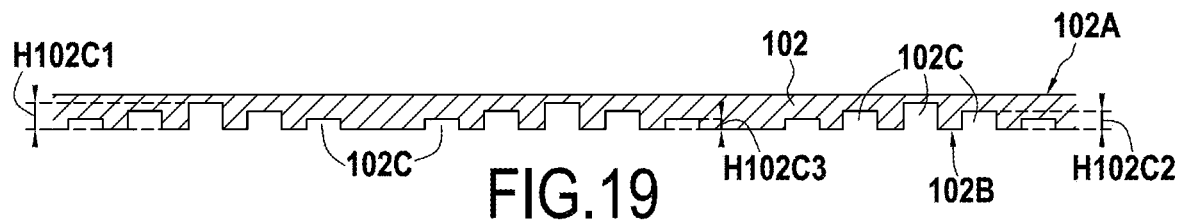
FIG. 19 shows a partial schematic cross-sectional view according to the plane XIX-XIX of the molding strip to form the pattern of FIG. 18.

FIGS. 15 to 19, which are similar views to the view in FIG. 12, show other patterns formed by the cavities 102C of the molding strips 102. FIG. 19 is a similar view to the view in FIG. 14 for the pattern in FIG. 18. As can be seen, the cavities 102C are not continuous and do not have a uniform depth. The cavities 102C have three different heights H102C1, H102C2, H102C3.

Figure 15:
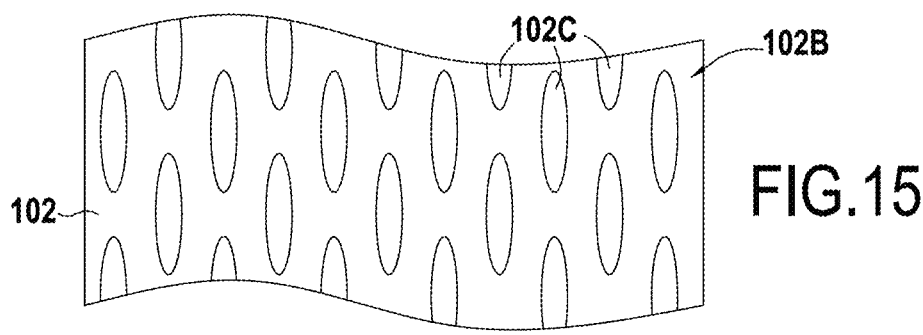
FIGS. 15-18 are schematic views of molding strip patterns according to other embodiments.

For example, the anti-slip strip 34 obtained by distributing elastomeric material with the molding strip 102 in FIG. 15 is an anti-slip strip with a width L34A measured in the lateral direction Y equal to 20 mm. Taking the full width L34A of the anti-slip strip, a zone of 110 mm$^2$ comprises 11 protruding elements 34B, i.e. a density of 10 protruding elements per cm$^2$, representing 25.15% of the total area of the base 34A.

Figure 16:
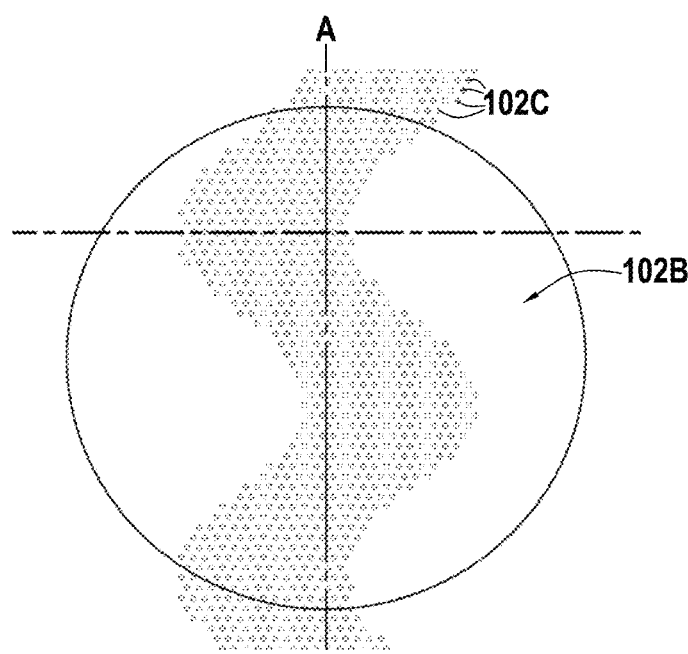

For example, the anti-slip strip 34 obtained by distributing elastomeric material with the molding strip 102 in FIG. 16 is an anti-slip strip with a width L34A measured in the lateral direction Y equal to 20 mm. Taking the full width L34A of the anti-slip strip, a zone of 382.78 mm$^2$ comprises 225 protruding elements 34B, i.e. a density of 58.78 protruding elements per cm$^2$, representing 8.11% of the total area of the base 34A.

For example, the anti-slip strip 34 obtained by distributing elastomeric material with the molding strip 102 in FIG. 17 is an anti-slip strip with a width L34A measured in the lateral direction Y equal to 20 mm. Taking the full width L34A of the anti-slip strip, a zone of 251.66 mm$^2$ comprises 405 protruding elements 34B, i.e. a density of 160.93 protruding elements per cm$^2$, representing 9.91% of the total area of the base 34A.

For example, the anti-slip strip 34 obtained by distributing elastomeric material with the molding strip 102 in FIG. 18 is an anti-slip strip with a width L34A measured in the lateral direction Y equal to 20 mm. Taking the full width L34A of the anti-slip strip, a zone of 187.35 mm$^2$ comprises 35 protruding elements 34B, i.e. a density of 18.682 protruding elements per cm$^2$, representing 25.22% of the total area of the base 34A.

Figure 29:
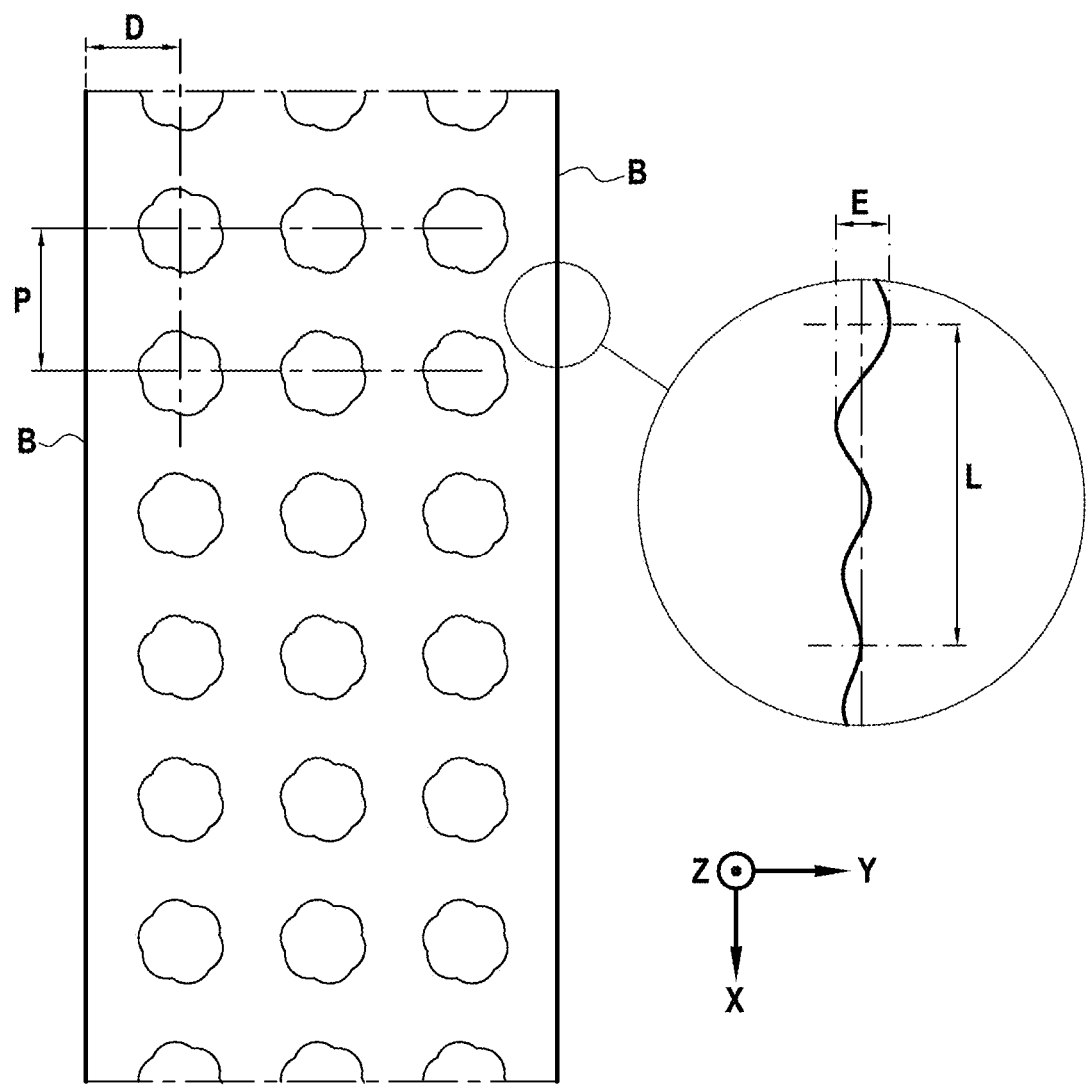
FIG. 29 is a top view of an anti-slip strip illustrating the edge properties of this strip.

As shown in FIG. 29, the anti-slip strip 34 is obtained by injecting elastomeric material into the molding strip 102, so the anti-slip strip 34 extends in the longitudinal direction X in FIG. 29. The lateral direction Y is also shown in FIG. 29. Here the longitudinal direction X is parallel to the machine direction MD, i.e. the direction of travel of the anti-slip strip 34.

Two edges B are defined for this anti-slip strip 34, each extending in the longitudinal direction X, these two edges B defining the two ends of the base 34A of the anti-slip strip 34 in the lateral direction Y, orthogonal to the longitudinal direction X.

The protruding elements are generally arranged close to the edges B, for example at a distance D from the edges B comprised between 2 and 3 pitches P of protruding elements, typically equal to 2 or 3 pitches P, the distance D being measured in the lateral direction Y in relation to the longitudinal direction X. The pitch P between two protruding elements corresponds to the distance between two successive protruding elements in the longitudinal direction. In the example shown in FIG. 29, the protruding elements are arranged in columns extending in the longitudinal direction X, these columns being repeated identically in the lateral direction Y. The protruding elements may also be arranged in a staggered or "honeycomb" arrangement, for example by shifting the columns of the protruding elements in the longitudinal direction.

As shown in FIG. 29, each of the edges B has a succession of hills and valleys, said succession extending in the longitudinal direction L and said hills and valleys extending in a plane parallel to that formed by the base 34A of the anti-slip strip 34, said hills and valleys reflecting slight irregularities in the distribution of molding material for the formation of the anti-slip strip 34, it being understood that a perfectly straight edge is not industrially feasible.

Valleys are understood to be the regions of the edges B protruding inwardly from the anti-slip strip 34, whereas hills are understood to be the regions of the edges B protruding outwardly from the anti-slip strip 34.

The regularity of the edges B may thus be evaluated by virtue of these successive hills and valleys.

The edges B have, when viewed in section in a direction transverse to the longitudinal direction, a portion with a rounded shape. In particular, the rounded shape is oriented to the lateral outside of the base 34A. This rounded shape is produced when forming the base 34A. In other words, this rounded shape was not obtained by cutting.

The apparatus and the process as presented above make it possible to obtain edges B of the anti-slip strip 34 such that for a length L in the longitudinal direction L corresponding to three consecutive hills, the maximum distance E between the hills and valleys in the lateral direction Y, orthogonal to the longitudinal direction X is less than 3 mm, or more precisely less than 2 mm, or more precisely less than 1 mm, or comprised between 0.001 mm and 1 mm, more particularly between 0.001 mm and 0.5 mm, more particularly between 0.001 mm and 0.1 mm.

Such a definition is also applicable for a length corresponding to three consecutive valleys; the maximum distance between the hills and the valleys in the lateral direction Y is less than 3 mm, or more precisely less than 2 mm, or more precisely less than 1 mm, or comprised between 0.001 mm and 1 mm, more particularly between 0.001 mm and 0.5 mm, more particularly between 0.001 mm and 0.1 mm.

The 3 consecutive hills or valleys are typically less than the distance corresponding to 15 steps P of protruding elements, preferably less than a distance of 25 mm.

It is advantageous to obtain "straight" edges B, as this eliminates the need for a subsequent edge straightening step, for example a cutting step, as such straight edges are perceived by the user as a sign of product quality.

Furthermore, the equipment and the process used make it possible to obtain such straight edges without the need for extra thicknesses at the edge of the tape, as such extra thicknesses are of no functional interest.

As can be understood from the above description, the straight edges are obtained by injecting the molding material through the material distribution means 106. Subsequent demolding and forming steps retain these straight edges as described above, as long as these steps do not result in the application of forces to the edges of the base 34A of the anti-slip strip 34. The anti-slip strip 34 thus obtained at the end of these various steps therefore has a straight edge as defined above.

For measurements of the coefficient of static friction, residual deformation and elongation at break, the measurement specimens are prepared in a similar manner and according to the method described below.

The laminated assembly is conditioned in a normal atmosphere, as defined in ASTM D5170, at a temperature of 23° C.±2° C. and a relative humidity of 50%±5% for 24 hours.

The coefficient of static friction is measured, in accordance with ASTM D1894, by moving a 200 g (gram) pad with an area of 63 mm×63 mm at a speed of 150 mm/min (millimeters per minute) over the surface of the anti-slip strip.

In the first part of the test, a specimen of the laminated assembly was attached to the friction table of the test system in an absolutely flat position using adhesive tape. The types of tape that may be used to adhere the material specimens to the friction table are well known to people with ordinary skills in the art and therefore will not be described in more detail in the present document.

In another part of the test, the front ear made of a Spunbond nonwoven (60 gsm PP (gram per square centimeter)) of the brand ULTRATEX D 1A 60× available from the firm "TEXBOND nonwovens" is positioned on the lower face of the pad facing the upper face of the specimen of the laminated assembly, with the calendered face of the Spunbond facing the upper face of the specimen of the laminated assembly. The pad is moved in translation on the specimen to be tested over at least a length of 15 mm enabling the value of the coefficient of static friction to be obtained.

For the measurement of the static coefficient of friction at 15% elongation, the specimen of the laminated assembly 30 is held at 15% elongation of the anti-slip strip 34 by double-sided adhesives. The measuring method is the same as for the measurement of the static coefficient of friction at rest.

For a specimen of a laminated assembly without a non-slip strip, for example a laminated assembly marketed under the name "High Stretch Surefit 100" with product number FM27R0140N010-AS02N, available from the firm "APLIX", the coefficient of static friction is 0.37 in the direction MD and 0.42 in the direction CD at rest.

For a laminated assembly comprising a High Stretch Surefit 100 support layer and an anti-slip strip obtained by means of the molding strip 102 of FIG. 9, the coefficient of static friction is 0.53 in the direction MD and 0.88 in the direction CD at rest and 0.73 in the direction MD and 0.99 in the direction CD when the specimen is stretched by 15% in the direction CD.

For a laminated assembly comprising a High Stretch Surefit 100 support layer and an anti-slip strip obtained by means of the molding strip 102 of FIG. 13, the coefficient of static friction is 0.71 in the direction MD and 1.06 in the direction CD at rest and 0.57 in the direction MD and 1.07 in the direction CD when the specimen is stretched by 15% in the direction CD.

For a laminated assembly comprising a High Stretch Surefit 100 support layer and an anti-slip strip obtained by means of the molding strip 102 of FIG. 15, the coefficient of static friction is 0.54 in the direction MD and 0.72 in the direction CD at rest and 0.79 in the direction MD and 0.84 in the direction CD when the specimen is stretched by 15% in the direction CD.

For measurements of residual deformation and elongation at break, the measuring equipment is a dynamometer according to EN 10002, for example Synergy 200H, 1 column available from MTS Systems Corp. in conjunction with TESTWORKS 4.04B user software.

Figure 25:
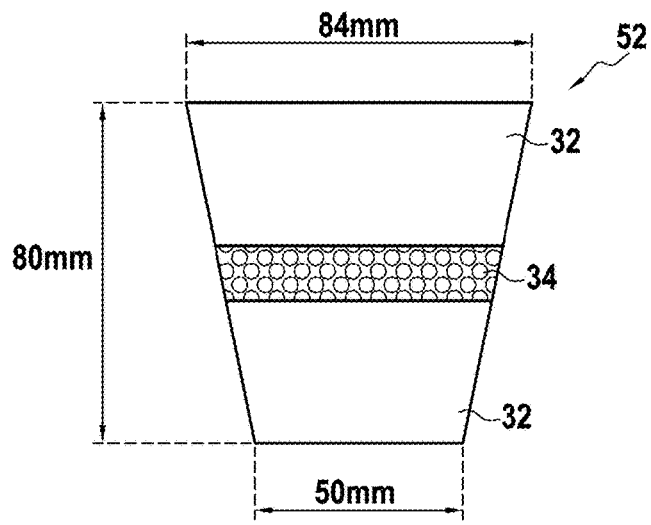
FIG. 25 is a schematic representation of a test specimen.

A specimen 52 is cut with a cutter or scissors to the desired shape, see FIG. 25. The specimen 52 has the general shape of an isosceles trapezium.

The anti-slip strip 34 has a length and a width. When the length of the anti-slip strip is parallel to the direction MD, the specimen 52 has a dimension of 80 mm in the direction CD. The small and large base of the isosceles trapezium are parallel to the direction MD and measure 50 mm and 84 mm respectively, as shown in FIG. 25.

Figure 26:
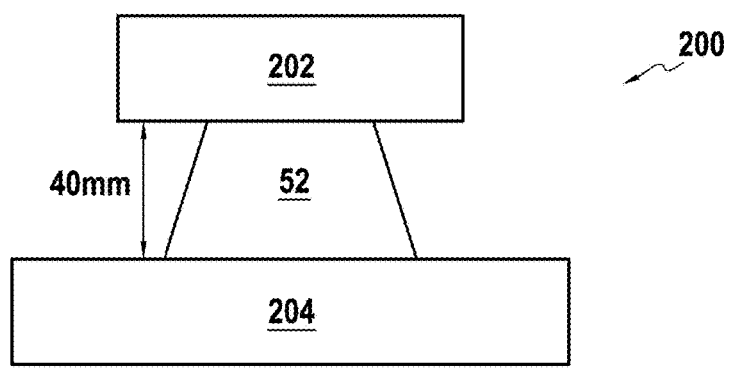
FIG. 26 is a schematic representation of a piece of equipment used to perform elongation at break and/or set measurement.

Each edge of the specimen 52 is reinforced with a reinforcement attached to the specimen with double-sided adhesive. Each reinforced edge of the specimen 52 is then placed in a jaw 202, 204 of the dynamometer 200 see FIG. 26). Before testing, the distance between the two jaws 202, 204 is 40 mm.

Elongation at break tests are carried out at a constant speed of movement of the jaws 202, 204 relative to each other. Generally, one jaw is fixed, here the lower jaw 204, and the other jaw is movable, here the upper jaw 202. To carry out the elongation at break test, the movable jaw is moved at a constant speed of 508 mm/min until the break is detected.

The elongation at break tests give the elongation at break at 10 N (newtons) expressed as a percentage of the initial size of the specimen 52 or in mm, the elongation at break expressed as a percentage of the initial size of the specimen 52 or in mm and the force at break expressed in N.

Figure 27:
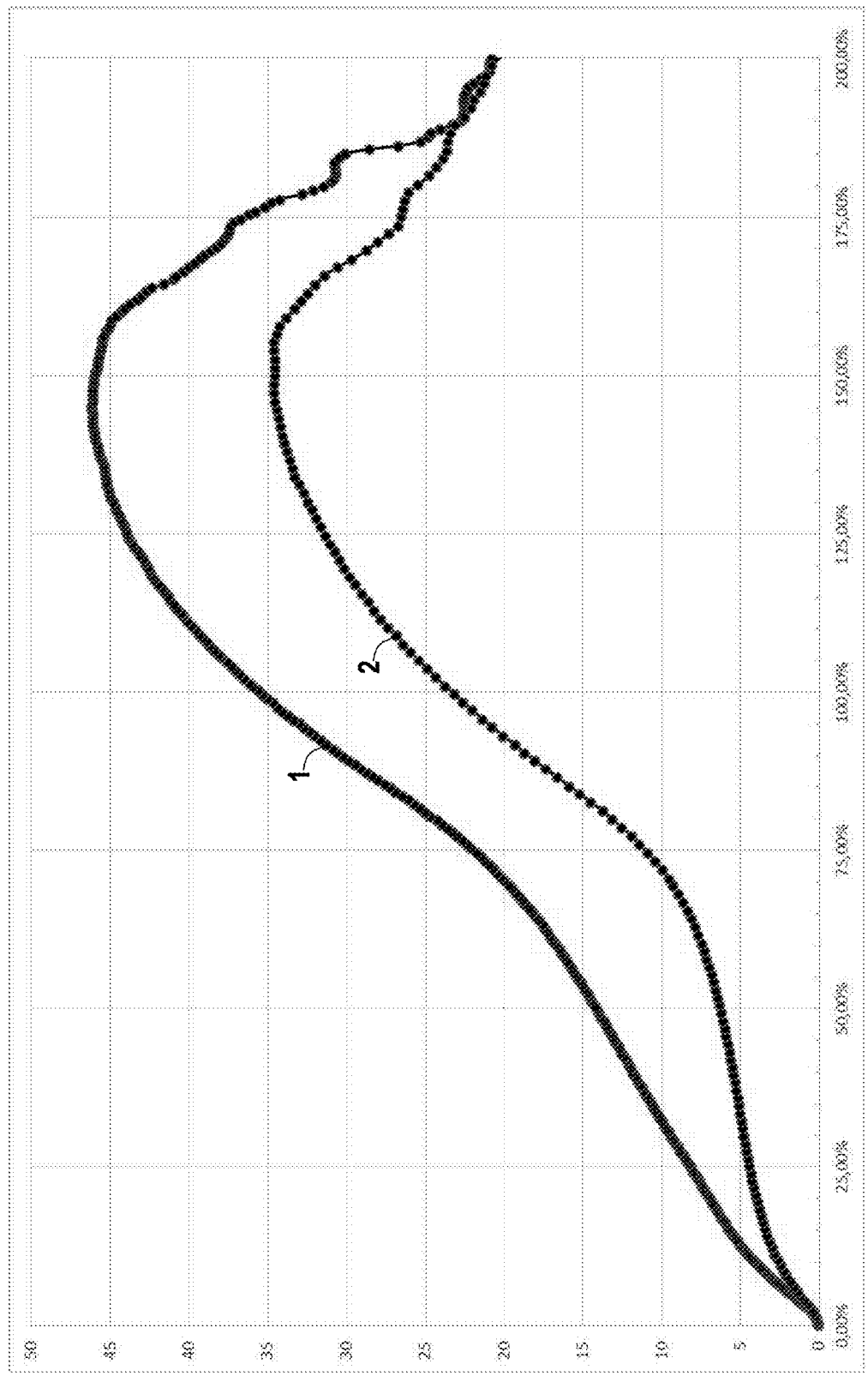
FIG. 27 is a graph representing the elongation at break curves of a laminated assembly including an anti-slip strip and a laminated assembly without such an anti-slip strip.

Elongation at break test curves are shown in FIG. 27. On the graph in FIG. 27, the x-axis represents the elongation expressed in percent of the original size of specimen 52 and the y-axis represents the force expressed in N. Curve 1 represents the elongation at break test for a laminated assembly including an anti-slip strip and Curve 2 represents the elongation at break test of the support layer of the laminated assembly of Curve 1, i.e. a laminated assembly without an anti-slip strip. It can be seen that the elongation at break is substantially similar for Curves 1 and 2. On the other hand, the force required to reach the rupture of the specimen 52 is greater when the support layer includes an anti-slip strip. For any elongation prior to the maximum force, the force obtained for a laminated assembly including an anti-slip strip is greater than the force obtained for a laminated assembly without an anti-slip strip.

Residual deformation tests are carried out with the same type of specimen as the specimens 52 of the elongation at break tests and on the same equipment.

The moving jaw has a constant speed of 508 mm/min, the initial jaw distance is 40 mm and the specimen is stretched until a force of 10 N is reached. Once the force of 10 N is reached, the movement of the movable jaw is stopped and the gap is maintained for 30 seconds. The jaw is then moved at constant speed to its starting position and the specimen 52 is held in this position for 60 seconds.

The result is a curve giving the stretching force expressed in N as a function of the elongation expressed in % of the initial specimen size. This curve has a hysteresis which allows the residual or SET deformation at the end of a cycle to be determined as follows: SET=point of intersection with the x-axis of the curve measured during the movement of the movable jaw when the movable jaw returns to its starting position, i.e. a jaw spacing of 40 mm.

Although the present disclosure has been described with reference to a specific example embodiment, it is obvious that various modifications and changes may be made to these examples without going beyond the general scope of the invention as defined by the claims. Furthermore, individual features of the different embodiments referred to may be combined in additional embodiments. Therefore, the description and drawings should be considered in an illustrative rather than restrictive sense. For example, the anti-slip strip may have a direction MD which is not parallel to the direction MD of the support layer. As an alternative embodiment of embodiments of FIGS. 2A to 8F, 20 to 25 and 28, it is possible to have studs and/or pins and/or stems surmounted by heads according to FIGS. 20 to 23 and/or stems surmounted by heads according to FIG. 28.

The invention claimed is:

1. A laminated assembly for a hygiene article comprising a support layer and an anti-slip strip, the anti-slip strip comprising an elastomeric material, the support layer and the anti-slip strip being laminated together, the anti-slip strip comprising a base and a plurality of protruding elements extending from the base and the plurality of protruding elements protruding from a face of the laminated assembly, wherein the anti-slip strip is free of openings.

2. The laminated assembly according to claim 1, wherein the support layer comprises a nonwoven web.

3. The laminated assembly according to claim 1, wherein the support layer comprises a thermoplastic film.

4. The laminated assembly according to claim 1, wherein the support layer comprises an elastic film comprising a thermoplastic material, the base of the anti-slip strip and the elastic film each having a width, the width of the base being less than the width of the elastic film.

5. The laminated assembly according to claim 4, wherein the width of the base is greater than or equal to 10% of the width of the elastic film and less than or equal to 60% of the width of the elastic film.

6. The laminated assembly according to claim 1, wherein the support layer comprises a first nonwoven web, a second nonwoven web and an elastic film comprising a thermoplastic material, the elastic film being laminated between the first and second nonwoven webs.

7. The laminated assembly according to claim 1, wherein, at rest, in a zone comprising the protruding elements, the anti-slip strip has a coefficient of static friction, measured according to standard ASTM D1894, in a machine direction and/or a direction perpendicular to the machine direction, greater than or equal to 0.1 and less than or equal to 10.

8. The laminated assembly according to claim 7, wherein, at rest, in the zone comprising the protruding elements, the anti-slip strip has a coefficient of static friction, measured according to standard ASTM D1894, in the direction MD and/or the direction CD, greater than or equal to 0.8 and less than or equal to 3.

9. The laminated assembly according to claim 1, wherein the anti-slip strip has a coefficient of static friction, measured according to standard ASTM D1894, when the anti-slip strip is stretched to 15% of a rest value, comprised between 50% and 150% of the coefficient of static friction at rest.

10. The laminated assembly according to claim 1, wherein, at rest, the plurality of protruding elements has a protruding element density greater than or equal to 3 protruding elements per $cm^2$, and less than or equal to 400 protruding elements per $cm^2$.

11. The laminated assembly according to claim 10, wherein, at rest, the plurality of protruding elements has a protruding element density greater than or equal to 10 protruding elements per cm$^2$, and less than or equal to 300 protruding elements per cm$^2$.

12. The laminated assembly according to claim 1, wherein, at rest, the plurality of protruding elements have a pattern comprising a repetition of a slip-resistant strip pattern.

13. The laminated assembly according to claim 1, wherein a sum of areas defined on the base by orthogonal projections of protruding elements on the base is greater than or equal to 1% of the total area of the base of an anti-slip strip pattern, and less than or equal to 40% of the total area of the base of the anti-slip strip pattern.

14. The laminated assembly according to claim 13, wherein the sum of the areas defined on the base by the orthogonal projections of protruding elements on the base is greater than or equal to 5% of the total area of the base of the anti-slip strip pattern, and less than or equal to 35% of the total area of the base of the anti-slip strip pattern.

15. The laminated assembly according to claim 1, wherein the base has a thickness greater than or equal to 10 μm, and less than or equal to 200 μm.

16. The laminated assembly according to claim 1, wherein the protruding elements are pins and/or studs and/or stems, each stem having a head disposed at an end of the stem opposite the base.

17. An absorbent article comprising a laminated assembly according to claim 1.

18. The laminated assembly of claim 1, wherein the anti-slip strip comprises a thermoplastic elastomeric material.

19. The laminated assembly of claim 1, wherein a width of the base is less than a width of an elastic film of the support layer, the elastic film is present in a portion of an elastic ear of the hygiene article, and a length of the base is greater than the width of the base.

20. A process for manufacturing a laminated assembly for a hygiene article, the process comprising following steps:
    forming an anti-slip strip comprising a base and a plurality of protruding elements extending from the base by distributing an elastomeric material in a molding device;
    assembling a support layer and the anti-slip strip by laminating the support layer and the anti-slip strip, wherein the anti-slip strip is free of openings.

* * * * *